(12) United States Patent
Farinas

(10) Patent No.: US 7,045,305 B1
(45) Date of Patent: May 16, 2006

(54) METHODS AND REAGENTS FOR TARGETING ORGANIC COMPOUNDS TO SELECTED CELLULAR LOCATIONS

(75) Inventor: Javier Farinas, Los Altos, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/403,882

(22) PCT Filed: Apr. 8, 1999

(86) PCT No.: PCT/US99/07847

§ 371 (c)(1),
(2), (4) Date: Mar. 20, 2000

(87) PCT Pub. No.: WO99/51986

PCT Pub. Date: Oct. 14, 1999

Related U.S. Application Data

(60) Provisional application No. 60/081,340, filed on Apr. 9, 1998, provisional application No. 60/081,118, filed on Apr. 8, 1998.

(51) Int. Cl.
*G01N 33/53* (2006.01)
*C12N 15/13* (2006.01)
*C12P 21/08* (2006.01)
*C07H 21/04* (2006.01)

(52) U.S. Cl. ............... 435/7.21; 435/320.1; 530/387.3; 536/23.1

(58) Field of Classification Search ............. 435/320.1, 435/6, 7.2, 7.21, 328; 530/387.3, 388.9, 530/38; 536/23.1
See application file for complete search history.

(56) References Cited

U.S. PATENT DOCUMENTS

| | | | |
|---|---|---|---|
| 4,618,827 A | | 10/1986 | Redington |
| 5,324,502 A | * | 6/1994 | Green et al. |
| 5,328,984 A | | 7/1994 | Pastan et al. |
| 5,561,049 A | | 10/1996 | Vold et al. |
| 5,602,095 A | | 2/1997 | Pastan et al. |
| 5,608,039 A | * | 3/1997 | Pastan et al. |
| 5,628,982 A | * | 5/1997 | Lauffer et al. |
| 5,703,369 A | | 12/1997 | Mori |
| 6,017,754 A | * | 1/2000 | Chesnut et al. |

FOREIGN PATENT DOCUMENTS

WO        93/11120 A1  *  6/1993

OTHER PUBLICATIONS

Haugland et al., Handbook of Flurescent Probes and Research Chemicals 6th edition, 1996, pp. 13-15, 18-19.*
Rizzuto et al, Current Biology 5(6): 635-642, 1995.*
Youn et al Analytical Biochemistry 232: 24-30, 1995.*
Skolnick et al, From genes to protein structure and function: novel applications of computational approaches in the genomic era, Jan. 2000, Trends in Biotech. 18(1): 34-39.*
Ngo et al, 1994, The Protein Folding Problem and Tertiary Structure Prediction, pp. 492-495.*
Abaza et al, J Protein Chemistry 11(5): 433-444, 1992.*
Schouten et al, Plan Mol Biol 30(4): 781-93, Feb. 1996.*
Kneen et al, Biophysical J 74: 1591-1599, Mar. 1998.*
Winkler et al, J Immunology 165: 4505-4514, 2000.*
Richardson, Jennifer, H. et al, "Phenotypic knockout of the high-affinity human interleukin 2 receptor by intracellular single-chain antibodies against the α subunit of the receptor", *Proc. Natl. Acad. Sci,.* 92, 3137-3141, 1995.
Yuan, Olan et al, "Intracellular single-chain antibody inhibits integrin VLA-4 maturation and function", *Biochem J.,* 318, 591-596, 1996.

* cited by examiner

*Primary Examiner*—Christina Chan
*Assistant Examiner*—Phuong N Huynh
(74) *Attorney, Agent, or Firm*—DLA Piper Rudnick Gray Cary US LLP

(57) ABSTRACT

The present invention provides methods and reagents for targeting probes to selected cellular locations, through the expression of specific binding partners to that probe within the cell. In one embodiment, the probes may comprise spectroscopic probe that can be used in a method for localizing a specific binding partner within a cell, and for creating assays for post-translational activities. The invention allows the monitoring of the location of such intracellular specific binding partners over time and in response to stimuli, such as test chemicals. The spectroscopic probes can be used for screening a test chemical for activity. The present invention also includes cells and transgenic organisms comprising the intracellular specific binding partner, wherein the specific binding partner can bind with the spectroscopic probe/ligand conjugate.

20 Claims, 4 Drawing Sheets

METHODS AND REAGENTS FOR TARGETING ORGANIC COMPOUNDS TO SELECTED CELLULAR LOCATIONS

This application is filed under 35 U.S.C. 371(e) from PCT/US99/07847 filed Apr. 8, 1999, which claims priority from U.S. provisional application Ser. Nos. 60/081,118 filed Apr. 8, 1998 and 60/081,340 filed Apr. 9, 1998, all of which are incorporated by reference in their entirety.

This invention was made in part with Government support under grant nos. DK43840 and DK35124 awarded by the National Institutes of Health. The Government may have rights in this invention.

FIELD OF THE INVENTION

The present invention is directed to membrane permeant compounds that have an organic compound coupled to a ligand and methods of localizing and using such compounds as spectroscopic probes, or reagents.

BACKGROUND OF THE INVENTION

Studies on intact living tissues and cells often require the introduction of reagents or spectroscopic probes into the cells in order to provide a specific stimulus or to measure a particular cellular function. Such approaches are typically improved in both selectivity and sensitivity if the reagents or spectroscopic probes can be targeted to specific locations within a cell or organism. For example, the selective targeting of spectroscopic probes within a cell enables defined measurements of subcellular microenvironments such as within subcellular organelles to be precisely probed. The use of spectroscopic probes tagged to macromolecules enables spatio-temporal aspects of a tagged macromolecule to be monitored in real time in vivo. Such methods can be used to develop a variety of specific assays for cellular activation, or to create functional assays of enzymatic function. For example, the location of a nuclear receptor within a cell can be determined by creating a fusion protein of the receptor to a specific binding partner and then observing its movement, after addition of a fluorescent ligand for the specific binding partner, in response to a test stimulus, such as a chemical. In this example, activation of nuclear receptor results in their translocation into the nucleus, which can be used as an assay to determine the relative activity of a series of different chemicals.

In transgenic organisms the targeting of NMR contrast agents or positron emission probes enables whole organism imaging of specific tissues or cell types in the intact organism.

In spite of the many advantages of this approach there are few general methods of labeling macromolecules, such as proteins with organic compounds within intact living organisms, that are specific and selective enough to be of practical utility. Traditionally, labeling of proteins or polypeptides has been accomplished by chemical modification of purified proteins. For example, the normal procedures for fluorescent labeling required that the polypeptide be covalently reacted in vitro with a fluorescent dye then re-purified to remove excess dye and/or any damaged polypeptide. Using this approach, problems of labeling stoichiometry and disruption of biological activity are often encountered. Furthermore, the analysis of a chemically modified polypeptide within a cell, typically requires microinjection, or other means, to introduce the peptide into the cell. These methods are relatively inefficient, damaging to cells and not readily amenable to large numbers of cells, typically used for high throughput screening.

By contrast, the present invention provides a targeting method that combines the ability to genetically encoded a protein sequence, and specifically express that sequence within living cells, with the use of well characterized spectroscopic probes or other probes. The invention thus enables the use of a wide range of fluorophores, as well as other spectroscopic probes, including nuclear magnetic resonance (NMR), positron emission tomography (PET), relaxation reagents, chromophores, and other reagents such as chemical cross linkers, caged compounds, enzymatic substrates, activators and substrates to be selectively targeted within intact cells or organisms.

These advantages enable a range of whole cell based assays to be developed that provide specific advantages over, and are complementary with, existing methods of fluorescence analysis or in vivo labeling. For example, the utility of green fluorescent protein (GFP) based measurements are limited to fluorescence based measurements only. Furthermore, highly fluorescent GFP mutants are only available within a limited range of excitation and emission maxima, and typically have poorer fluorescent properties compared to the best small molecule fluorophores.

The use of FLASH, an arseno-fluorescein derivative, involves the addition of a membrane permeant arseno-fluorescein derivative to the cells that binds to a short alpha helix containing 4 cysteines that can be added to a protein of interest (Griffin, et al., (1998) Science 281 269–72). At present the FLASH approach is limited to a single fluorophore, however in combination with the present invention both methods may be used to specifically label two proteins with two different fluorophores.

In one embodiment, the invention provides for the intracellular expression of a high affinity specific binding partner that specifically interacts with a fluorophore-coupled ligand. In a preferred embodiment the specific binding partner comprises a single chain antibody (sFv) as the specific binding partner, and a hapten (phOx) as the ligand.

SUMMARY OF THE INVENTION

The present invention is directed towards methods and uses of targeted probes in living organisms or cells. In one embodiment, the probe is a spectroscopic probe moiety coupled to a ligand to create a spectroscopic probe/ligand conjugate that can be localized to a specific binding partner within an organism. In one aspect, the specific binding partner is a single chain antibody, which specifically binds to the spectroscopic probe/ligand conjugate. In another aspect, the compound is membrane permeant and is useful for localizing the spectroscopic probe/ligand conjugate to intracellular structures comprising a high affinity specific binding partner for the fluorescent ligand within a living cell. In another aspect, the organic molecule is substantially non-membrane permeable, and the specific binding partner is attached to the extracellular face of the plasma membrane. The spectroscopic probes may be detected using a variety of techniques including fluorescence, nuclear magnetic resonance and positron emission tomography.

One embodiment of the method further comprises the step of adding a stimulus to the cell and comparing the intracellular spatial distribution of the specific binding partner fusion protein, before, and after addition of the stimulus. In one aspect this method further comprises the step of adding a test chemical to determine if it can modulate the effect of the stimulus.

In another embodiment, the method involves detecting post-translational activity using a specific binding partner fusion protein/spectroscopic probe/ligand conjugate expressed within a cell. In one aspect, the method involves detecting said spectroscopic probe/ligand conjugate before and after activation of a post-translational activity within the cell. In one aspect, this method involves visualizing the localization, or detecting a fluorescent property, of said spectroscopic probe/ligand conjugate, such as fluorescence emission, polarization or fluorescence lifetime. In another aspect, detecting involves NMR imaging or positron emission tomography. In one aspect of this method, the method further comprises the step of adding a test chemical to determine if it can modulate the effect of post-translational activation.

In one aspect, the invention is an expression vector comprising expression control sequences operatively linked to a nucleic acid sequence encoding a specific binding partner for a spectroscopic probe/ligand conjugate fused to a protein of interest and a fluorescent protein. In one aspect of this embodiment, the spectroscopic probe moiety and the fluorescent protein change position relative to each upon post-translational modification of the protein of interest.

In one aspect the invention is an expression vector comprising expression control sequences operatively linked to a nucleic acid sequence encoding a specific binding partner for a spectroscopic probe/ligand conjugate fused to a protein of interest and a protein comprising a second specific binding domain for a second fluorescent moiety. In one aspect of this embodiment, the spectroscopic probe moiety and the second fluorescent moiety change position relative to each upon post-translational modification of the protein of interest.

In another aspect the invention includes a host cell transfected with a specific binding partner fused to another protein. In another aspect, the invention features a transgenic non-human animal having a phenotype characterized by expression of the nucleic acid sequence coding for the expression of the specific binding partner. The phenotype is conferred by a transgene contained in the somatic and germ cells of the animal. The animal can be a mouse.

A further aspect of the present invention is a method of screening a test chemical for an activity using a cell comprising a nucleic acid encoding a specific binding partner having a binding region that binds a spectroscopic probe/ligand conjugate. In some embodiments, the nucleic acid molecule encoding the specific binding partner may be randomly integrated into the genome or operably linked to a response element or promoter element.

In one embodiment, the specific binding partner is a protein or polypeptide that is adapted to bind to the fluorescent ligand with high affinity within the cell. In one aspect the protein is selected from a random pool of proteins expressed in a plurality of cells containing a diverse population of randomly arranged sequences. In one aspect the polypeptide comprises a single chain antibody. In one aspect of this embodiment, the single chain antibody is adapted for functional expression within the reducing environment of one or more subcellular compartments of a mammalian cell.

In another embodiment, the invention provides a method for localizing a probe, comprising contacting a sample comprising a cell expressing a specific binding partner with a probe/ligand conjugate, said probe/ligand conjugate, said probe/ligand conjugate comprising a probe moiety, a ligand that can bind with said specific binding partner, and a linker moiety coupling said probe to said ligand, wherein said ligand and said specific binding partner bind non-covalently, wherein said probe/ligand conjugate is membrane permeant, and wherein the specific binding partner is expressed from a recombinant nucleic acid.

In another embodiment, the invention provides a method for detecting a post-translational activity in a cell, comprising contacting a cell expressing a specific binding partner fused to a protein of interest with a spectroscopic probe/ligand conjugate, said spectroscopic probe/ligand conjugate comprising a spectroscopic probe moiety, a ligand that can bind with said specific binding partner, and a linker moiety coupling said spectroscopic probe to said ligand, activating said post-translational activity in said cell, and detecting said spectroscopic probe/ligand conjugate, before and at least one time after activation of said post-translational activity, wherein said ligand and said specific binding partner bind non-covalently, wherein said probe/ligand conjugate is membrane permeant, and wherein the specific binding partner is expressed from a recombinant nucleic acid.

In another invention, the invention provides a method of screening a test chemical for activity, comprising contacting a cell with a test chemical, said cell comprising, a nucleic acid encoding a specific binding partner, said specific binding partner comprising, a binding region which binds a spectroscopic probe/ligand conjugate, contacting said cell with a spectroscopic probe/ligand conjugate, said spectroscopic probe/ligand conjugate comprising (1) a spectroscopic probe moiety, (2) a ligand that can bind with said specific binding partner, and a linker moiety coupling said spectroscopic probe to said ligand, and detecting said spectroscopic probe/ligand conjugate, wherein said ligand and said specific binding partner bind non-covalently, wherein said probe/ligand conjugate is membrane permeant, and wherein the specific binding partner is expressed from a recombinant nucleic acid.

BRIEF DESCRIPTION OF THE DRAWINGS

FIG. 2C shows the excitation and emission spectra of phOx-fluorescein (1 nM) in PBS (solid line). Spectra of an identical concentration of sFv-bound phOx-fluorescein (dashed line) measured in sFv-containing CHO cell suspension. FIG. 2D. shows the phOx-fluorescein fluorescence at indicated concentrations in regions of an image without cells (filled squares), regions in non-sFv expressing cells (triangles), and regions in cells expressing sFv at the plasma membrane (circles). The fluorescence of sFv bound phOx-fluorescein was fitted to a single site binding model (dashed line) with $K_d$ 6.8 nM.

FIG. 3A is a confocal image of CHO cells transfected with the plasma membrane-targeted sFv vector and shows plasma membrane staining by phOx-rhodamine. FIG. 3B is a confocal fluorescence image of the cells in FIG. 3A stained with a fluorescein-labeled anti-c-myc antibody. FIG. 3C shows the brightfield image of the cells in FIG. 3A. FIG. 3D shows a fluorescence image of CHO cells with Golgi-targeted sFv in the presence of 10 nM phOx-Bodipy®F1. FIG. 3E shows the same cells as in FIG. 3D in the presence of 500 nM phOx-ethanolamine and 10 nM phOx-Bodipy®FL. FIG. 3F is a fluorescence image of a cell with ER-targeted sFv in the presence of 10 nM phOx-Bodipy®. FIG. 3G shows immunostaining of Golgi-sFv transfected cells with fluorescein labeled, anti-c-myc antibody. FIG. 3H shows immunostaining of Golgi-sFv transfected cells with rhodamine-labeled anti-mouse antibody directed against a mouse 58 k protein antibody. FIG. 3I shows immunostaining of ER-sFv transfected cells with rhodamine-labeled anti-mouse antibody directed against an anti-c-myc antibody. FIG. 3J shows immunostaining of ER-sFv transfected cells with fluorescein-labeled concavalin A. The scale bar represents 10 micrometers.

FIG. 4A shows the average ratio generated by pixel-by-pixel division of 490 nm images by 440 nm images after background subtraction. The ratio was converted to pH using a calibration relating pH to fluorescence signal ratios for Golgi (circles) and plasma membrane (squares) targeted phOx-fluorescein. Plasma membrane data was acquired in the presence of 10 nM phOx-fluorescein. The ratios of absorbance at 490-to-440 nm are shown for unbound phOx-fluorescein (triangles) in solution. Calibration data were fitted to a single site titration model (fluorescence solid line, absorbance dashed line). FIG. 4B represents the fluorescence ratio (490/440) time course in Golgi. At indicated times, bafilomycin $A_1$ (100 nM) and high $K^+$ buffers (120 mM) containing 5 µM monensin at indicated pH were added. Calibration solutions were used to convert ratios to pH values (scale at right). FIG. 4C represents the calculated pH time course in response to a 20 mM sodium acetate pre-pulse in the absence and presence of 100 nM bafilomycin $A_1$. Lines (fitted from 120 to 300 seconds after pre-pulse) indicate the initial rate of pH change. FIG. 4D represents the calculated proton pump rates (circles) and leak rates (filled squares) as a function of Golgi pH. Dashed lines are linear fits to the data.

DETAILED DESCRIPTION

Definitions

Figure 1:
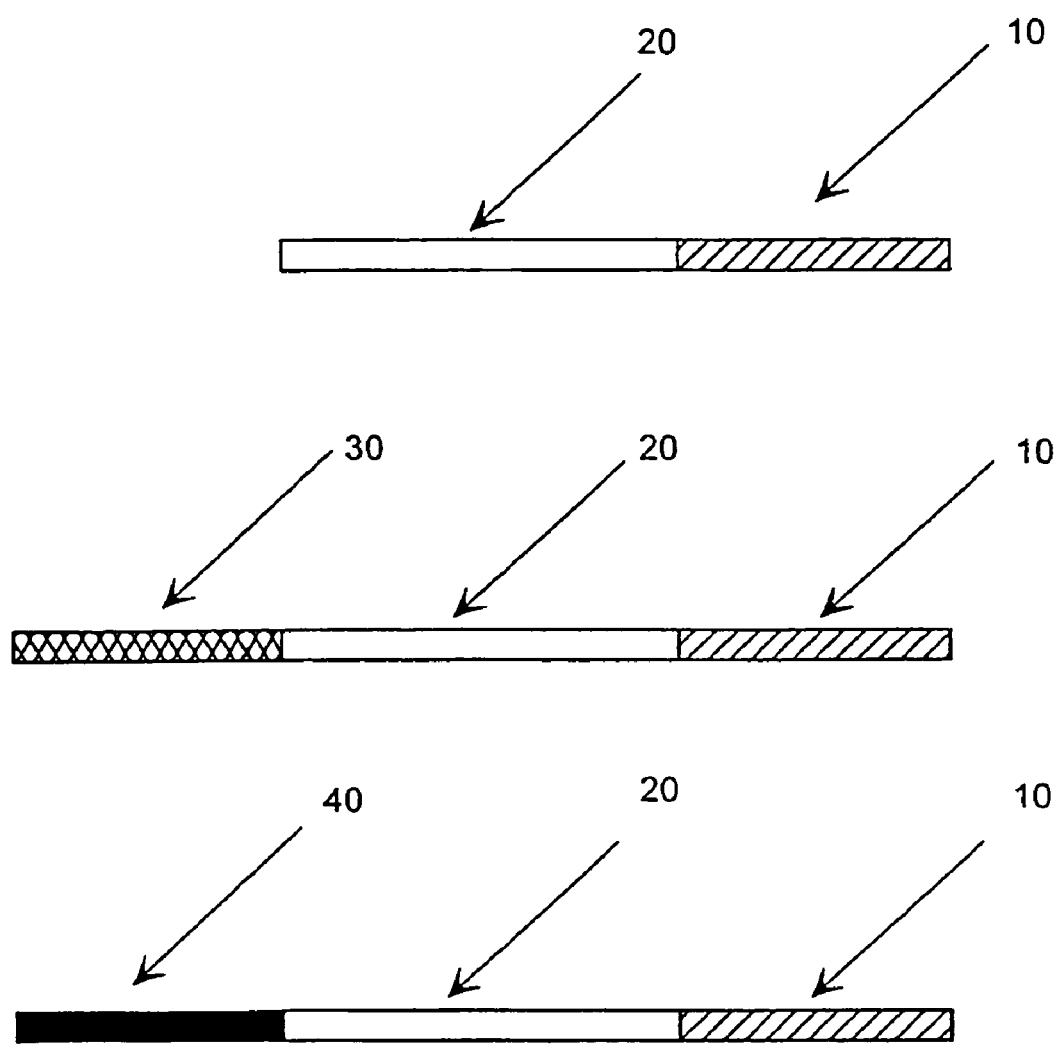
FIG. 1 represents a schematic representation of several embodiments of the specific binding partners of the present invention. In one embodiment, the specific binding partner (10) is fused in frame with a protein of interest (20). The protein of interest typically comprises cellular location motifs that can direct the fusion protein to specific subcellular locations as described herein. In a further embodiment, the fusion of interest (20) is fused to a fluorescent protein or homologue thereof (30). In another embodiment, the protein of interest is fused to a second specific binding partner (40) that recognizes a distinct ligand.

Unless defined otherwise, all technical and scientific terms used herein have the same meaning as commonly understood by one of ordinary skill in the art to which this invention belongs. Generally, the nomenclature used herein and many of the fluorescence, computer, detection, chemistry and laboratory procedures described below are those well known and commonly employed in the art. Standard techniques are usually used for chemical synthesis, fluorescence, optics, molecular biology, computer software and integration. Generally, chemical reactions, cell assays and enzymatic reactions are performed according to the manufacturer's specifications where appropriate. The techniques and procedures are generally performed according to conventional methods in the art and various general references. (Lakowicz, J. R. *Topics in Fluorescence Spectroscopy*, (3 volumes) New York: Plenum Press (1991), and Lakowicz, J. R. *Emerging applications of fluorescence spectroscopy to cellular imaging: lifetime imaging, metal-ligand probes, multi-photon excitation and light quenching*. Scanning Microsc Suppl Vol. 10 (1996) pages 213–24, for fluorescence techniques; Sambrook et al. *Molecular Cloning: A Laboratory Manual*, 2d ed. (1989) Cold Spring Harbor Laboratory Press, Cold Spring Harbor, N.Y., for molecular biology methods; *Cells: A Laboratory Manual*, $1^{st}$ edition (1998) Cold Spring Harbor Laboratory Press, Cold Spring Harbor, N.Y., for cell biology methods; *Optics Guide 5* Melles Griot® Irvine Calif., and *Optical Waveguide Theory*, Snyder & Love published by Chapman & Hall for general optical methods, which are incorporated herein by reference which are provided throughout this document).

As employed throughout the disclosure, the following terms, unless otherwise indicated, shall be understood to have the following meanings:

The term "polypeptide" refers to a polymer in which the monomers are amino acids and are joined together through amide bonds, alternatively referred to as a peptide. Additionally, unnatural amino acids, for example, beta-alanine, phenylglycine and homoarginine are also meant to be included. Commonly encountered amino acids, which are not gene-encoded, may also be used in the present invention. For a general review see Spatola, A. F., in *Chemistry and Biochemistry of Amino Acids, Peptides and Proteins*, B. Weinstein, eds., Marcel Dekker, New York, p. 267 (1983). All of the amino acids used in the present invention may be either the D- or L-isomer. The L-isomers are preferred. Chemically modified amino acids, for example including phosphorylated, sulfated, methylated, or prenylated residues may also be used to create polypeptides for specific applications.

The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "probe" refers to a compound useful as marker or environmental indicator, or modifying reagent for use with the present invention. Probes may comprises fluorescent, spectroscopic or modifying moieties as described herein.

The term "spectroscopic probe or moiety" refers to a compound that can be used as a marker or indicator, or contrast agent for nuclear magnetic resonance imaging, positron emission tomography, absorption spectroscopy, luminescence spectroscopy and fluorescence spectroscopy.

The term "fluorescent probe or moiety" refers to a compound that can absorb electromagnetic energy and is capable of at least partially remitting some fraction of that energy as electromagnetic radiation over some time period. Suitable fluorescent moieties include, but are not limited to, coumarins and related dyes, xanthene dyes such as fluoresceins, rhodols, and rhodamines, resorufins, cyanine dyes, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, semiconductor fluorescent nanocrystals, fluorescent proteins and fluorescent europium and terbium complexes and related compounds.

Fluorescent moieties may also be environmental sensitive or be indicators of various ions such as calcium, magnesium or pH, as is known in the art.

The term "modifying moiety" refers to compounds that can modify the function of a protein or macromolecule within the cell. Examples of modify moieties include but are not limited to chemical cross linkers, caged compounds, enzymatic substrates, activators and inhibitors.

The term "optical property" refers to the molar extinction coefficient at an appropriate excitation wavelength, the fluorescent quantum efficiency, the shape of the excitation spectrum or emission spectrum, the excitation wavelength maximum or emission wavelength maximum, the ratio of excitation amplitudes at two different wavelengths, the ratio of emission amplitudes at two different wavelengths, the excited state lifetime, the fluorescent anisotropy or any other measurable property of a compound.

The term "post-translational activity" refers to activities that mediate a modification of a protein such that its activity, function or cellular localization is changed. Such modifications include phosphorylation, glycosylation, methylation, sulfation, ubiquitination, proteolysis, prenylation and ADP-ribsoylation. The term includes non-covalent modifications including protein—protein interactions, and the binding of allosteric or other modulators or second messengers such as calcium, cAMP or inositol phosphates to a protein of interest.

The term "specific binding partner" refers to a member of a specific binding pair as that term is known in the art. Specific binding pairs include, for example, antigen-antibody, hapten-antibody, receptor-ligand, nucleic acid-nucleic acid, nucleic acid-protein, enzyme-inhibitor and enzyme-substrate pairs. The interaction between specific binding pairs can be covalent or non-covalent in nature. Specific binding members can be of any chemical composition, such as protein, carbohydrate, lipid, chemical, nucleic acid or any combination thereof.

The term "acceptor" refers to a quencher that operates via energy transfer. Acceptors may re-emit the transferred energy as fluorescence and are "acceptor fluorescent moieties". Examples of acceptors include coumarins and related fluorophores, xanthenes such as fluoresceins, rhodols, and rhodamines, resorufins, cyanines, difluoroboradiazaindacenes, and phthalocyanines. Other chemical classes of acceptors generally do not re-emit the transferred energy. Examples include indigos, benzoquinones, anthraquinones, azo compounds, nitro compounds, indoanilines, and di- and triphenylmethanes.

The term "homologue" refers to two sequences or parts thereof, that are greater than, or equal to 75% identical when optimally aligned using the ALIGN program. Homology or sequence identity refers to the following. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of more than 5 (in standard deviation units) using the program ALIGN with the mutation data matrix and a gap penalty of 6 or greater. See Dayhoff, M. O., in *Atlas of Protein Sequence and Structure,* 1972, volume 5, National Biomedical Research Foundation, pp. 1 01–1 10, and Supplement 2 to this volume, pp. 1–1 0.

The following terms are used to describe the sequence relationships between two or more polynucleotides: "reference sequence," "comparison window," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA or gene sequence given in a sequence listing such as a SEQ ID NO:1, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48:443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 30 percent sequence identity, preferably at least 50 to 60 percent sequence identity, more usually at least 60 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least 30 percent sequence identity, preferably at least 40 percent sequence identity, more preferably at least 50 percent sequence identity, and most preferably at least 60 percent sequence identity. Preferably, residue positions, which are not identical, differ by conservative amino acid substitutions. Conservative amino acid substitutions refer to the interchangeability of residues having similar side chains. For example, a group of amino acids having aliphatic side chains is glycine, alanine, valine, leucine, and isoleucine. A group of amino acids having aliphatic-hydroxyl side chains is serine and threonine. A group of amino acids having amide-containing side chains is asparagine and glutamine. A group of amino acids having aromatic side chains is phenylalanine, tyrosine, and tryptophan. A group of amino acids having basic side chains is lysine, arginine, and histidine. A group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

The term "test chemical" refers to a chemical to be tested by one or more screening method(s) of the invention as a putative modulator. A test chemical can be any chemical, such as an inorganic chemical, an organic chemical, a protein, a peptide, a carbohydrate, a lipid, or a combination thereof. Usually, various predetermined concentrations of test chemicals are used for screening, such as 0.01 micromolar, 1 micromolar and 10 micromolar. Test chemical controls can include the measurement of a signal in the absence of the test compound or comparison to a compound known to modulate the target.

"Membrane permeant" means that a compound can pass through a membrane, such as a cell membrane, such as a eukaryotic cell membrane, preferably a mammalian cell membrane. Preferably, membrane permeant compounds pass through a membrane without the assistance of transport molecules within a membrane, such as porins, but the present invention recognizes such transport molecules as a mechanism of membrane permeability of compounds. Substantially membrane permeant means that a compound can pass through a membrane and accumulate within a cell to a concentration useful in the methods of the present invention, such as the detection of intracellular specific binding members using fluorescent detection methods. Preferably, the compound is at lest as membrane permeable as CCF2/AM (as described in U.S. Pat. No. 5,741,657 issued Apr. 21, 1998 to Tsien et al).

"Membrane-permeant derivative" refers a chemical derivative of a compound of that increases membrane permeability of the compound. These derivatives are made better able to cross cell membranes, i.e. membrane permeant, because hydrophilic groups are masked to provide more hydrophobic derivatives. Also, the masking groups are designed to be cleaved from the fluorogenic substrate within the cell to generate the derived substrate intracellularly. Because the substrate is more hydrophilic than the membrane permeant derivative it becomes trapped within the cell.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

"Control sequence" refers to polynucleotide sequences which are necessary to effect the expression of coding and non-coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, components whose presence can influence expression, and can also include additional components whose presence is advantageous, for example, leader sequences and fusion partner sequences.

The term "nucleic acid" refers to a polymeric form of nucleotides of at least ten bases in length, either ribonucleotides or deoxynucleotides or a modified form of either type of nucleotide. The term includes single and double stranded forms of DNA.

"Modulation" refers to the capacity to either enhance or inhibit a functional property of a biological activity or process (e.g., enzyme activity or receptor binding). Such enhancement or inhibition may be contingent on the occurrence of a specific event, such as activation of a signal transduction pathway, and/or may be manifest only in particular cell types.

The term "modulator" refers to a chemical (naturally occurring or non-naturally occurring), such as a biological macromolecule (e.g. nucleic acid, protein, non-peptide, or organic molecule), or an extract made from biological materials such as bacteria, plants, fingi, or animal (particularly mammalian) cells or tissues. Modulators are typically evaluated for potential activity as inhibitors or activators (directly or indirectly) of a biological process or processes (e.g., agonist, partial antagonist, partial agonist, antagonist, antineoplastic agents, cytotoxic agents, inhibitors of neoplastic transformation or cell proliferation, cell proliferation-promoting agents, and the like) by inclusion in assays described herein. The activity of a modulator may be known, unknown or partial known. Other chemistry terms herein are used according to conventional usage in the art, as exemplified by The McGraw-Hill Dictionary of Chemical Terms (ed. Parker, S., 1985), McGraw-Hill, San Francisco, incorporated herein by reference).

Introduction

The present invention recognizes that a probe can be coupled to a ligand, to create a probe/ligand conjugate that is useful for a range of cell based assays. Typically the probe/ligand conjugate of the present invention is used in conjunction with an intracellular specific binding member or receptor, that specifically binds to the probe/ligand conjugate. The specific binding partner is typically a protein or polypeptide, and in one preferred embodiment is a single chain antibody. Typically, the specific binding partner can be part of a fusion protein that comprises a known or unknown protein of interest, so that the intracellular specific binding member localizes with the protein of interest. Upon binding of the probe/ligand conjugate, the intracellular localization of the specific binding partner and fusion protein can be located and monitored in a living cell. Additionally a variety of detection methods can be used to provide information on the post-translational modification state and interactions of a fusion protein comprising a protein of interest, coupled to a specific binding partner.

Spectroscopic Probe Moieties

The choice of the spectroscopic probe moiety is governed by a number of factors including, the type of measurements being made, the availability of specific instrumentation and the ease of coupling of the probe moiety to the hapten. Additionally, other factors that are specific to a particular application are also relevant and include, the effect of labeling on the solubility of the ligand, permeability of the probe/ligand conjugate across the plasma membrane, the stability of the conjugate within the cell and the required detection sensitivity of the assay.

For fluorescent probes, preferred fluorophores typically exhibit good quantum yields, lifetimes, and extinction coefficients, are resistant to collisional quenching and bleaching, and should preferably be easily conjugated to the ligand. Particularly desirable, are fluorophores that show absorbance and emission in the red and near infrared range, which are useful in whole animal studies, because of reduced scattering background fluorescence, and greater transmission through tissues. Examples of such moieties include cyanines, oxazines, thiazines, porphyrins, phthalocyanines, fluorescent infrared-emitting polynuclear aromatic hydrocarbons such as violanthrones, and near IR squaraine dyes. (For example as shown in Dyes and Pigments, 17 19–27 (1991), U.S. Pat. No. 5,631,169 to Lakowicz et al., issued May 20, 1997, and organo-metallic complexes such as the ruthenium and lanthanide complexes of U.S. Pat. Nos. 4,745,076 and 4,670,572, the disclosures of which are incorporated herein by reference). The lanthanide complexes have the advantage of not being quenched by oxygen, and the long lifetimes may allow easy suppression of the autofluorescence of biological samples. Specific materials include fluoroscein isothicyanate (especially fluorescein-5 isothiocyanate), dichlorotriazinylaminofluorescein, tetramethylrhodamine-5 (and -6)-isothiocyanate, 1,3-bis-(2-dialkylamino-5-thienyl)-substituted squarines, and the succinimidyl esters of: 5 (and 6) carboxyfluoroscein; 5 (and 6)-carboxytetramethylrhodamine; and 7-amino-4-methylcoumarin-3-acetic acid.

For positron emission tomography, preferred spectroscopic probes include lipophilic cationic complexes of radioactive metal ions such as gallium-68 (III) with metal chelating ligands, as described in U.S. Pat. No. 5,324,502, issued Jun. 28, 1994 to Green et al., and carbon-11 containing compounds as described in J. Nucl. Med. 38 1305–10 (1997).

Preferred spectroscopic probes for use as NMR contrast agents include chelates of paramagnetic, ferromagnetic or diamagnetic metal ions complexed to lipophilic complexes as described in U.S. Pat. No. 5,628,982, issued May 13, 1997 to Lauffer et al. and U.S. Pat. No. 5,242,681, issued Sep. 7, 1993 to Elgavish et al., and fluorine-18- and 19 containing compounds J. Nucl. Med. 39 1884–91 (1998).

In many applications it is desirable to derivatize the compounds above to render them more hydrophobic and permeable through cell membranes. The derivatizing groups should undergo hydrolysis inside cells to regenerate the compounds thus trapping them within cells. For this purpose, it is preferred that any phenolic hydroxyls or free amines in the dye structures are acylated with $C_1$–$C_4$ acyl groups (e.g. formyl, acetyl, n-butryl) or converted to various esters and carbonates, as described in Bundgaard, H., Design of Prodrugs, Elsevier Science Publishers (1985), Chapter 1, page 3 et seq., Further modification of the fluorescent moieties may also be accomplished, as required as described in U.S. Pat. No. 5,741,657 issued Apr. 21, 1998 to Tsien et al.

The spectroscopic probe is generally attached by a linker that provides a spacer between the spectroscopic probe and the ligand thereby preventing sterric interference of the spectroscopic probe on the ligand specific binding partner interaction. Preferred spacers are substantially stable under cellular conditions, non ionic and easily coupled to the ligand and spectroscopic probe. Preferred examples include flexible aliphatic linkers such as diaminopentane, and aminohexanoyl as well as rigid aromatic linkers such as trans cyclohexane. Such linkers are know in the art and described for example in the *Handbook of Fluorescent Probes and Research Chemicals*, by Richard Haugland, published by Molecular Probes.

Specific Binding Partners

Typically the specific binding partner or receptor for use in the present invention is a polypeptide or protein that can bind to high affinity to the spectroscopic probe/ligand conjugate. In one case the specific binding partner comprises a single chain antibody that exhibits high specificity and selectivity for the probe/ligand conjugate. In one embodiment, the single chain antibody is essentially as described in Griffith et al. (1984) Nature 312 271–275 (SEQ ID NOs: 1–2). The single chain antibody may also comprise one or more antibody recognition motifs fused in frame with the coding sequence for immunological confirmation of specific binding partner expression. For example the hemagglutinin, Poly His, V5 or myc epitopes are well characterized and monoclonal antibodies in each case are commercially available. (Evans et al. (1985) Mol. Cell. Biol. 5 3610–3616). Other single chain antibodies can be produced to recognize distinct haptens using methods well known in the art, for example as disclosed in European patent EP 0 589 877 B 1. The term "single chain antibody" includes single chain antibodies with separate light and heavy chains co-expressed in cells, and ioslated VH domains such as used for camelid antibodies as described in EMBO J. 9 101–102 (1990) and Prot. Eng. 9 531–7 (1996).

The specific binding partner can also include a localization sequence to direct the specific binding partner to particular cellular sites by fusion to appropriate organellar targeting signals or localized host proteins. A polynucleotide encoding a localization sequence, or signal sequence, can be ligated or fused at the 5' terminus of a polynucleotide encoding the specific binding partner such that the signal peptide is located at the amino terminal end of the resulting fusion polynucleotide/polypeptide. In the case of eukaryotes, the signal peptide is believed to function to transport the fusion polypeptide across the endoplasmic reticulum. The secretory protein is then transported through the Golgi apparatus, into secretory vesicles and into the extracellular space or, preferably, the external environment. Signal peptides, which can be utilized according to the invention, include pre-pro peptides that contain a proteolytic enzyme recognition site. Other signal peptides with similar properties to pro-calcitonin described herein are known to those skilled in the art, or can be readily ascertained without undue experimentation.

The localization sequence can be a nuclear localization sequence, an endoplasmic reticulum localization sequence, a peroxisome localization sequence, a mitochondrial localization sequence, or a localized protein. Localization sequences can be targeting sequences which are described, for example, in "Protein Targeting", chapter 35 of Stryer, L., *Biochemistry* (4th ed.). W. H. Freeman, 1995. The localization sequence can also be a localized protein. Some important localization sequences include those targeting the nucleus (SEQ ID NO:5) mitochondrion (amino terminal MLRTSSLFTRRVQPSLFRNILRLQST-SEQ ID NO:6), endoplasmic reticulum (KDEL at C-terminus, assuming a signal sequence present at N-terminus)(SEQ ID NO:7) , peroxisome (SKF at C-terminus), prenylation or insertion into plasma membrane (CaaX, CC, CXC, or CCXX (SEQ ID NO:6) at c-terminus), cytoplasmic side of plasma membrane (fusion to SNAP-25), or the Golgi apparatus (fusion to furin).

Additionally specific binding partners can be created by producing libraries of peptides containing a diverse population of amino acid sequences, and then screening the library to identify peptides that bind to the probe/ligand conjugate with high affinity. In one embodiment, a genetically engineered library of putative specific binding partners having a randomized sequence can be used to define a sequence that binds to a probe/ligand conjugate with high affinity.

As used herein, a "library" refers to a collection containing at least 5 different members, preferably at least 100 different members and more preferably at least 200 different members. The amino acid sequences for the peptide will typically be in the range or 10 to 20 amino acids in length and may be completely random or biased towards a particular sequence based on a particular structural motif, for example based on a known structure that has some binding affinity with the target ligand. In most instances the library will created genetically and the individual members expressed in bacterial or a mammalian cells.

For example, the library can contain peptides with a diverse collection of amino acids in which most or all of the amino acid positions are randomized. Alternatively, the library can contain variable peptide in which only a few, e.g., one to ten, amino acid positions are varied, but in which the probability of substitution is very high.

Preferably, libraries of peptides are created by expressing of recombinant nucleic acid molecules having expression control sequences operatively linked to nucleic acid sequences that code for the expression of different candidate specific binding partners. Methods of making nucleic acid molecules encoding a diverse collection of peptides are described in, for example, U.S. Pat. No. 5,432,018 (Dower et al.), U.S. Pat. No. 5,223,409 (Ladner et al.) and International patent publication WO 92/06176 (Huse et al.).

For expression of candidate specific binding partners, recombinant nucleic acid molecules are used to transfect cells, such that a cell contains on average one member of the library. This produces, in turn, a library of host cells capable of expressing a library of different candidate peptides. The library of host cells can then be used to screen for peptides that can bind to the spectroscopic probe/ligand conjugate.

In one method of creating such a library, a diverse collection of oligonucleotides having random codon sequences are combined to create polynucleotides encoding the candidate peptides. The oligonucleotides preferably are prepared by chemical synthesis. The polynucleotides encoding the peptides of variable composition can then be ligated to the 5' or 3' end of a nucleic acid encoding a defined gene, if required. For example, in one embodiment, they could be fused to a functional engineered green fluorescent protein. This creates a recombinant nucleic acid molecule coding for the expression of a variable peptide moiety fused to the amino or carboxy-terminus of a fluorescent protein. This recombinant nucleic acid molecule is then inserted into an expression vector to create a recombinant nucleic acid molecule comprising expression control sequences operatively linked to the sequences encoding the fluorescent protein fused to the variable peptide region.

To generate the collection of oligonucleotides which forms a series of codons encoding a random collection of amino acids that is ultimately cloned into the vector, a codon motif is used, such as $(NNK)_x$, where N may be A, C, G, or T (nominally equimolar), K is G or T (nominally equimolar), and x is the desired number of amino acids in the peptide moiety, e.g., 15 to produce a library of 15-mer peptides. The third position may also be G or C, designated "S". Thus, NNK or NNS (i) code for all the amino acids, (ii) code for only one stop codon, and (iii) reduce the range of codon bias from 6:1 to 3:1. The expression of peptides from randomly generated mixtures of oligonucleotides in appropriate recombinant vectors is discussed in Oliphant et al., *Gene* 44:177–183 (1986), incorporated herein by reference.

An exemplified codon motif $(NNK)_6$ produces 32 codons, one for each of 12 amino acids, two for each of five amino acids, three for each of three amino acids and one (amber) stop codon. Although this motif produces a codon distribution as equitable as available with standard methods of oligonucleotide synthesis, it results in a bias against peptides containing one-codon residues.

An alternative approach to minimize the bias against one-codon residues involves the synthesis of 20 activated tri-nucleotides, each representing the codon for one of the 20 genetically encoded amino acids. These are synthesized by conventional means, removed from the support but maintaining the base and 5-HO-protecting groups, and activating by the addition of 3'O-phosphoramidite (and phosphate protection with beta-cyanoethyl groups) by the method used for the activation of mononucleosides, as generally described in McBride and Caruthers, *Tetrahedron Letters* 22:245 (1983). Degenerate "oligocodons" are prepared using these trimers as building blocks. The trimers are mixed at the desired molar ratios and installed in the synthesizer. The ratios will usually be approximately equimolar, but may be a controlled unequal ratio to obtain the over- to under-representation of certain amino acids coded for by the degenerate oligonucleotide collection. The condensation of the trimers to form the oligocodons is done essentially as described for conventional synthesis employing activated mononucleosides as building blocks. See generally, Atkinson and Smith, *Oligonucleotide Synthesis*, M. J. Gait, ed. p 35–82 (1984). Thus, this procedure generates a population of oligonucleotides for cloning that is capable of encoding an equal distribution (or a controlled unequal distribution) of the possible peptide sequences.

Libraries of host cells expressing candidate peptides described above are then used in identifying peptide sequences that can bind to high affinity to the spectroscopic probe/ligand conjugate. In general, one begins with a library of recombinant host cells, each of which expresses a different peptide candidate specific binding partner. Each cell is expanded into a clonal population that is genetically homogeneous. The method consists of measuring the fluorescence of the cell after addition and incubation of the cell with the probe/ligand conjugate at a limiting concentration. Binding of the probe/ligand conjugate to the specific binding partner results in a net uptake of probe/ligand conjugate into the cell that can be readily measured over background non-specific uptake. Alternatively, in the case of fluorescent probes, specific binding can also be determined by measuring the degree of fluorescence energy transfer (FRET) between the fluorescent ligand conjugate and a fluorescent protein—peptide fusion protein. In this case, binding of the fluorescent ligand conjugate to the peptide fusion would result in an increase in FRET between the ligand and GFP. In both cases these events could be monitored using a fluorimeter, a 96 well plate reader, or by FACS (fluorescence Activated Cell Sorting) analysis and sorting.

The nucleic acids from cells exhibiting a change in FRET or enhancement in fluorescence as a result of fluorescent ligand binding can be isolated for example by PCR amplification, and the peptide sequences identified by sequencing. The results from these studies could used as the basis for the generation of more targeted libraries to identify optimal peptides through repeated rounds of analysis and selection of clones exhibiting the largest and most rapid changes in FRET in the presence, but not the absence of the fluorescent ligand conjugate.

Expression of the Specific Binding Partner within Cells

In one aspect, the method would involve the expression of the specific binding partner into living eukaryotic or prokaryotic cells as a fusion protein to a protein of interest to enable the subcellular localization of the protein to be determined. A variety of host-expression vector systems may be utilized to express the specific binding partner coding sequence. These include but are not limited to microorganisms such as bacteria transformed with recombinant bacteriophage DNA, plasmid DNA or cosmid DNA expression vectors containing a specific binding partner coding sequence; yeast transformed with recombinant yeast expression vectors containing the specific binding partner coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a specific binding partner coding sequence; insect cell systems infected with recombinant virus expression vectors (e.g., baculovirus) containing a specific binding partner coding sequence; or animal cell systems infected with recombinant virus expression vectors (e.g., retroviruses, adenovirus, vaccinia virus) containing a specific binding partner coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see, e.g., Bitter, et al., Methods in Enzymology 153:516–544, 1987). For example, when cloning in bacterial systems, inducible promoters such as pL of bacteriophage Σ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted specific binding artner coding sequence.

In bacterial systems a number of expression vectors may be advantageously selected depending upon the use intended for the specific binding partner expressed.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Methods in Enzymology, Eds. Wu & Grossman, 31987, Acad. Press, N.Y., Vol. 153, pp. 516–544, 1987; Glover, DNA Cloning, Vol. II, IRL Press, Wash., D.C. Ch. 3, 1986; and Bitter, Heterologous Gene Expression in Yeast, Methods in Enzymology, Eds. Berger & Kimmel, Acad. Press, N.Y., Vol. 152, pp. 673–684, 1987; and The Molecular Biology of the Yeast *Saccharomyces*, Eds. Strathern et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, IRL Press, Wash., D.C., 1986). Alternatively, vectors may be used which promote integration of foreign DNA sequences into the yeast chromosome.

In cases where plant expression vectors are used, the expression of a specific binding partner coding sequence may be driven by any of a number of promoters. For example, viral promoters such as the 35S RNA and 19S RNA promoters of CaMV (Brisson, et al., *Nature* 310: 511–514, 1984), or the coat protein promoter to TMV (Takamatsu, et al., *EMBO J.* 6:307–311, 1987) may be used; alternatively, plant promoters such as the small subunit of RUBISCO (Coruzzi, et al., 1984, *EMBO J.* 3:1671–1680; Broglie, et al., *Science* 224:838–843, 1984); or heat shock promoters, e.g., soybean hsp17.5-E or hsp17.3-B (Gurley, et al., *Mol. Cell. Biol.* 6:559–565, 1986) may be used. These constructs can be introduced into plant cells using Ti plasmids, $R_i$ plasmids, plant virus vectors, direct DNA transformation, microinjection, electroporation, etc. For reviews of such techniques see, for example, Weissbach & Weissbach, *Methods for Plant Molecular Biology*, Academic Press, NY, Section VIII, pp. 421–463, 1988; and Grierson & Corey, *Plant Molecular Biology*, 2d Ed., Blackie, London, Ch. 7–9, 1988.

An alternative expression system that could be used to express specific binding partner is an insect system. In one such system, *Autographa californica* nuclear polyhedrosis virus (AcNPV) is used as a vector to express foreign genes. The virus grows in *Spodoptera frugiperda* cells. The specific binding partner coding sequence may be cloned into non-essential regions (for example, the polyhedrin gene) of the virus and placed under control of an AcNPV promoter (for example the polyhedrin promoter). Successful insertion of the specific binding partner coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., *J. Viol.* 46:584, 1983; Smith, U.S. Pat. No. 4,215,051.

Mammalian cell systems that utilize recombinant viruses or viral elements to direct expression may be engineered. For example, when using adenovirus expression vectors, the specific binding partner coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the specific binding partner in infected hosts (e.g., see Logan & Shenk, *Proc. Natl. Acad. Sci. USA*, 81: 3655–3659, 1984). Alternatively, the vaccinia virus 7.5K promoter may be used. (e.g., see, Mackett, et al., *Proc. Natl. Acad. Sci. USA*, 79: 7415–7419, 1982; Mackett, et al., *J. Virol.* 49: 857–864, 1984; Panicali, et al., *Proc. Natl. Acad.*

Sci. USA 79: 4927–4931, 1982). Of particular interest are vectors based on bovine papilloma virus which have the ability to replicate as extrachromosomal elements (Sarver, et al., Mol. Cell. Biol. 1: 486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the specific binding partner gene in host cells (Cone & Mulligan, Proc. Natl. Acad. Sci. USA, 81:6349–6353, 1984). High level expression may also be achieved using inducible promoters, including, but not limited to, the metallothionine IIA promoter and heat shock promoters.

For long-term, stable expression of the specific binding partner within mammalian cells, host cells can be transformed with the specific binding partner cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., Cell, 11: 223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22: 817, 1980) genes can be employed in tk$^-$, hgprt$^-$ or aprt$^-$ cells respectively. Also, antimetabolite resistance can be used as the basis of selection for dhfr, which confers resistance to methotrexate (Wigler, et al., Proc. Natl. Acad. Sci. USA, 77: 3567, 1980; O'Hare, et al., Proc. Natl. Acad. Sci. USA, 8: 1527, 1981); gpt, which confers resistance to mycophenolic acid (Mulligan & Berg, Proc. Natl. Acad. Sci. USA, 78: 2072, 1981; neo, which confers resistance to the aminoglycoside G-418 (Colberre-Garapin, et al., J. Mol. Biol., 150:1, 1981); and hygro, which confers resistance to hygromycin (Santerre, et al., Gene, 30: 147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:8047, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

DNA sequences encoding the specific binding partner polypeptide of the invention can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

In another embodiment, the invention provides a transgenic non-human animal that expresses a nucleic acid sequence that encodes the specific binding partner. The "non-human animals" of the invention comprise any non-human animal having nucleic acid sequence which encodes a suitable specific binding partner. Such non-human animals include vertebrates such as rodents, non-human primates, sheep, dog, cow, pig, amphibians, and reptiles. Preferred non-human animals are selected from the rodent family including rat and mouse, most preferably mouse. Introducing "transgenes" into the germline of the non-human animal produces the "transgenic non-human animals" of the invention. Embryonic target cells at various developmental stages can be used to introduce transgenes. Different methods are used depending on the stage of development of the embryonic target cell. The zygote is the best target for microinjection. In the mouse, the male pronucleus reaches the size of approximately 20 micrometers in diameter that allows reproducible injection of 1–2 µl of DNA solution. The use of zygotes as a target for gene transfer has a major advantage in that in most cases the injected DNA will be incorporated into the host gene before the first cleavage (Brinster et al., Proc. Natl. Acad. Sci. USA 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

The term "transgenic" is used to describe an animal that includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals that include the exogenous genetic material within all of their cells in both alleles. 50% of the resulting animals will include the exogenous genetic material within one allele and 25% will include no exogenous genetic material. Retroviral infection can also be used to introduce transgene into a non-human animal. The developing non-human embryo can be cultured in vitro to the blastocyst stage. During this time, the blastomeres can be targets for retro viral infection (Jaenich, R., Proc. Natl. Acad. Sci USA 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., Proc. Natl. Acad. Sci. USA 82:6927–6931, 1985; Van der Putten, et al., Proc. Natl. Acad. Sci USA 82:6148–6152, 1985). Transfection is easily and efficiently obtained by culturing the blastomeres on a monolayer of virus-producing cells (Van der Putten, supra; Stewart, et al., EMBO J. 6:383–388, 1987). Alternatively, infection can be performed at a later stage. Virus or virus-producing cells can be injected into the blastocoele (D. Jahner et al., Nature 298:623–628, 1982). Most of the founders will be mosaic for the transgene since incorporation occurs only in a subset of the cells, which formed the transgenic nonhuman animal. Further, the founder may contain various retro viral insertions of the transgene at different positions in the genome that generally will segregate in the offspring. In addition, it is also possible to introduce transgenes into the germ line, albeit with low efficiency, by intrauterine retro viral infection of the midg-estation embryo (D. Jahner et al., supra).

A third type of target cell for transgene introduction is the embryonic stem cell (ES). ES cells are obtained from pre-implantation embryos cultured in vitro and fused with embryos (M. J. Evans et al. *Nature* 292:154–156, 1981; M. O. Bradley et al., *Nature* 309: 255–258, 1984; Gossler, et al., *Proc. Natl. Acad. Sci USA* 83: 9065–9069, 1986; and Robertson et al., *Nature* 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence that is transcribed into DNA and then incorporated into the genome. The transgenes of the invention include DNA sequences that encode the specific binding partner that may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

Methods of Measurement

Fluorescent methods that are preferred with the present invention include, time resolved fluorescence spectroscopy, fluorescence correlation spectroscopy, fluorescence polarization spectroscopy, and resonance energy based fluorescence spectroscopy. Methods of performing such assays on fluorescent materials are well known in the art and are described in, e.g., Lakowicz, J. R., *Topics in Fluorescence Spectroscopy*, volumes 1 to 3, New York: Plenum Press (1991); Herman, B., *Resonance energy transfer microscopy*, in: Fluorescence Microscopy of Living Cells in Culture, Part B, Methods in Cell Biology, vol. 30, ed. Taylor, D. L. & Wang, Y.-L., San Diego: Academic Press (1989), pp. 219–243; Turro, N. J., *Modern Molecular Photochemistry*, Menlo Park: Benjamin/Cummings Publishing Col, Inc. (1978), pp. 296–361.

Methods of NMR analysis are known in the art and described in U.S. Pat. No. 5,889,456, issued Mar. 30, 1999, U.S. Pat. No. 4,770,182, issued Sep. 13, 1988 and U.S. Pat. No. 4,618,827, issued Oct. 21, 1986. Positron emission tomography methods too are known in the art and described for example in U.S. Pat. No. 4,980,552, issued Dec. 25, 1990 and U.S. Pat. No. 5,703,369 issued Dec. 30, 1997. The methods of the present invention do not require the cell to be killed during the course of performing the analysis.

Fluorescent Assays

The present invention can be used to determine the expression and localization of the specific binding partner-fusion protein over time or after the cell has received a stimulus, such as being contacted with a test chemical. The method involves the creation of a fusion protein between the protein of interest and the specific binding partner, and the expression of the construct within a host cell, as described above. The addition of a fluorescent probe/ligand conjugate, as described in the Examples section below, results in the specific fluorescent labeling of the specific binding partner fusion protein. Analysis of the cell by fluorescent microscopy reveals the subcellular distribution of the protein of interest, prior to the addition of the stimulus. The subsequent subcellular distribution of the protein of interest may then subsequently be assessed during or after stimulation of the cell, for example by exposure of the cell to an agonist, antagonist or test chemical.

In one embodiment, the specific binding partners are randomly integrated into the host cells genome in order to tag unknown genes. For example, the nucleic acid molecule can integrate into the genome of the host cell and expression can be modulated by expression control elements or promoters contained within the genome using gene trapping or promoter trapping techniques (see, PCT/US97/17395) or as described above. In this embodiment, the specific binding partner can be used to monitor the induction, repression and spatial localization of a particular protein.

In one embodiment the specific binding partners may be expressed on the extracellular surface of the cell, within a transgenic organism in order to enable the spatial distribution of a particular cell type or tissue to be analyzed.

In other aspect the present invention can be used to develop assays for post-translational modifications such as proteolysis, phosphorylation and protein—protein interactions of the protein of interest fused to specific binding partner. The method used to determine the degree of post-translational modification of the protein of interest is dependent on the assay format used.

In one aspect, the method may be based on the difference in fluorescence anisotropy of the fluorescent ligand/specific binding partner-fusion protein complex before and after exposure to a stimulus. In this case modification of the protein of interest, by the post translational activity in response to stimulation of the cell, results in a change in the rotational flexibility of the complex that results in a measurable change in fluorescence polarization of the fluorescent specific binding partner/ligand complex. As shown in FIG. 1 the method involves the creation of a fusion protein between the specific binding partner and the protein of interest that contains a site of post-translational modification. For example in the case of proteolysis, the protein of interest would contain a proteolysis site. In this case, proteolysis would result in the cleavage of the protein of interest resulting an increase in rotational movement of the fluorophore. Alternatively in the case of a protein—protein interaction assays, protein binding to the protein of interest, as a result of phosphorylation, or otherwise would result in a decrease in rotational flexibility. In either case, the resulting change in rotational flexibility would influence the florescence anisotropy of the fluorescent ligand/specific binding partner-fusion protein complex.

Polarization measurements are based on the relative rotational movement of the fluorophore compared to the excited state life-time of that fluorophore. For globular molecules in dilute solution, the relationship between polarization (p) and the degree of rotational movement can be readily derived (see Weber, *Polarization of the fluorescence of solutions*, in Fluorescence and Phosphorescence Analysis, Don Hercules (ed.), Interscience Publishers New York. Chapter 8, pages 217–240 (1966)). Rotational movement can be related to the rotational diffusion constant of the molecule, and hence to the molecular volume. In practice there is a close correlation between the molecular size and relative polarization of emitted light from a fluorophore. As a consequence, a significant change in fluorescence polarization can occur when the fluorescent substrates of the present invention are acted upon by a protease. Polarization based measurements are relatively easy to set up, and can be obtained over a wide concentration, temperature, and ionic strength range.

In another aspect, the present invention takes advantage of fluorescence resonance energy transfer (FRET) between two fluorescent moieties to provide a ratiometric fluorescent readout. In this embodiment (FIG. 1), the specific binding partner typically comprises a second fluorescent moiety, for example by the creation of a fusion protein between a fluorescent protein or second fluorescent moiety and the protein of interest and the specific binding partner. In this case, cleavage of the protein of interest by a protease results in an alteration in energy transfer between the specific binding partner bound fluorescent ligand and the fluorescent protein or second fluorescent moiety that may be used to detect protease activity. In this case, the fluorescent moieties are typically chosen such that the excitation spectrum of one of the moieties (the acceptor fluorescent moiety) overlaps with the emission spectrum of the donor fluorescent moiety. The selection and use of specific fluorophores or quenchers for particular applications is known in the art, for example see, Berlman, I. B. *Energy transfer parameters of aromatic compounds*, Academic Press, New York and London (1973), that contains tables of spectral overlap integrals for the selection of resonance energy transfer partners. Additional information sources include Tsien et al., 1990 *Handbook of Biological Confocal Microscopy* pp. 169–178. The donor fluorescent moiety is excited by light of appropriate intensity within the donor fluorescent moiety's excitation spectrum and under conditions in which direct excitation of the acceptor fluorophore is minimized. The donor fluorescent moiety then transfers the absorbed energy by non radiative means to the acceptor, which subsequently re-emits some of the absorbed energy as fluorescence emission, at a characteristic wavelength. FRET can be manifested as a reduction in the intensity of the fluorescent signal from the donor, reduction in the lifetime of its excited state, and an increase in emission of fluorescence from the acceptor fluorescent moiety. When the peptide substrate that connects the donor fluorescent moiety and acceptor fluorescent moiety is cleaved, the donor fluorescent moiety and the acceptor fluorescent moiety physically separate, and FRET is diminished or eliminated. Under these circumstances fluorescence emission from the donor increases and fluorescence emission from the acceptor decreases.

The efficiency of FRET is dependent on the separation distance and the orientation of the donor fluorescent moiety and acceptor fluorescent moiety, the fluorescent quantum yield of the donor moiety and the energetic overlap with the acceptor moiety. Forster derived the relationship:

$$E = (F^0 - F)/F^0 = R_0^6/(R^6 + R_0^6)$$

where E is the efficiency of FRET, F and $F^0$ are the fluorescence intensities of the donor in the presence and absence of the acceptor, respectively, and R is the distance between the donor and the acceptor. $R_0$, the distance at which the energy transfer efficiency is 50%, is given (in Å) by $$R_0 = 9.79 \times 10^3 (K^2 Q J n^{-4})^{1/6}$$

where $K^2$ is an orientation factor having an average value close to 0.67 for freely mobile donors and acceptors, Q is the quantum yield of the unquenched fluorescent donor, n is the refractive index of the intervening medium, and J is the overlap integral, which expresses in quantitative terms the degree of spectral overlap, $$J = \int \circ_0 F^4 d / \int \circ_0 F d$$

where is the molar absorptivity of the acceptor in $M_{-1}$ cm$^{-1}$ and F is the donor fluorescence at wavelength measured in cm. Forster, T. (1948) Ann. Physik 2:55–75. The characteristic distance $R_0$ at which FRET is 50% efficient depends on the quantum yield of the donor, the extinction coefficient of the acceptor, the overlap between the donor's emission spectrum and the acceptor's excitation spectrum and the orientation factor between the two fluorophores.

Preferably, changes in the degree of FRET are determined as a function of the change in the ratio of the amount of fluorescence from the donor and acceptor moieties, a process referred to as "ratioing." By calculating the ratio, the assay is insensitive to fluctuations in substrate concentration, photobleaching and excitation intensity making the assay more robust. This is of particular importance in automated screening applications where the quality of the data produced is important for its subsequent analysis and interpretation.

In one aspect the method would involve a fusion protein comprising a peptide containing one or more binding sites for a second fluorescent moiety (FIG. 1). For example, the binding site could comprises a sequence that recognizes a fluorescent moiety as described in the pending U.S. patent applications, identified by Ser. No. 08/955,050, filed Oct. 21, 1997, entitled Methods of using synthetic molecules and target sequences; Ser. No. 08/955,859, filed Oct. 21, 1997, entitled Synthetic molecules that specifically react with target sequences, and Ser. No. 08/955,206, filed Oct. 21, 1997, entitled Target sequences for synthetic molecules. In this case, expression of the specific binding partner fusion protein and binding site could be accomplished recombinantly as described above. The addition of the membrane permeate fluorescent moieties capable of binding to the binding site and specific binding partner would enable the creation, in situ of a fluorescent substrate capable of detecting proteolysis. Alternatively the binding sites for the second fluorescent moiety could be created through the fusion to a second specific binding partner that recognized a distinct ligand.

In another aspect the second fluorescent moiety is a fluorescent protein (FIG. 1). Such fluorescent proteins include endogenously fluorescent proteins, functional engineered fluorescent proteins, and homologues thereof, because the entire fluorophore and specific binding partner can be synthesized within intact living cells without the addition of other co-factors or fluorophores (for review see Cubitt et al, TIBS 20, pp. 448–455 1995). Endogenously fluorescent proteins have been isolated and cloned from a number of marine species including the sea pansies *Renilla reniformmis*, *R. kollikeri* and *R. mullerei* and from the sea pens *Ptilosarcus*, *Stylatula* and *Acanthoptilum*, as well as from the Pacific Northwest jellyfish, *Aequorea Victoria*; Szent-Gyorgyi et al. (SPIE conference 1999), D. C. Prasher et al., Gene, 111:229–233 (1992). These proteins are capable of forming a highly fluorescent, intrinsic chromophore through the cyclization and oxidation of internal amino acids within the protein that can be spectrally resolved from weakly fluorescent amino acids such as tryptophan and tyrosine.

Additionally fluorescent proteins have also been observed in other organisms, although in most cases these require the addition of some exogenous factor to enable fluorescence development. For example, the cloning and expression of yellow fluorescent protein from *Vibrio fischeri* strain Y-1 has been described by T. O. Baldwin et al., Biochemistry (1990) 29:5509–15. This protein requires flavins as fluorescent co-factors. The cloning of Peridinin-chlorophyll a binding protein from the dinoflagellate *Symbiodinium* sp. was described by B. J. Morris et al., Plant Molecular Biology, (1994) 24:673:77. One useful aspect of this protein is that it fluoresces in red. The cloning of phycobiliproteins from marine cyanobacteria such as *Synechococcus*, e.g., phycoerythrin and phycocyanin, is described in S. M. Wilbanks et al., J. Biol. Chem. (1993) 268:1226–35. These proteins require phycobilins as fluorescent co-factors, whose insertion into the proteins involves auxiliary enzymes. The proteins fluoresce at yellow to red wavelengths.

A variety of mutants of the GFP from *Aequorea Victoria* have been created that have distinct spectral properties, improved brightness and enhanced expression and folding in mammalian cells compared to the native GFP, Table 1, (Tsien review, U.S. Pat. No. 5,625,048 to Tsien et al., issued Apr. 29, 1997; U.S. Pat. No. 5,777,079 to Tsien et al., issued Jul. 7, 1998; and U.S. Pat. No. 5,804,387 to Cormack et al., issued Sep. 8, 1998). In many cases these functional engineered fluorescent proteins have superior spectral properties to wild-type *Aequorea* GFP and are preferred for use in the fluorescent substrates of the invention.

TABLE 1

| Mutations | Common Name | Quantum Yield (Φ) & Molar Extinction (ε) | Excitation & Emission Max | Relative Fluorescence At 37° C. | Sensitivity To Low pH % max F at pH 6 |
|---|---|---|---|---|---|
| S65T type | | | | | |
| S65T, S72A, N149K, M153T, I167T | Emerald | Φ = 0.68 ε = 57,500 | 487 509 | 100 | 91 |
| F64L, S65T, V163A | | Φ = 0.58 ε = 42,000 | 488 511 | 54 | 43 |
| F64L, S65T (EGFP) | EGFP | Φ = 0.60 ε = 55,900 | 488 507 | 20 | 57 |
| S65T | | Φ = 0.64 ε = 52,000 | 489 511 | 12 | 56 |
| Y66H type | | | | | |
| F64L, Y66H, Y145F, V163A | P4-3E | Φ = 0.27 ε = 22,000 | 384 448 | 100 | N.D. |
| F64L, Y66H, Y145F | | Φ = 0.26 ε = 26,300 | 383 447 | 82 | 57 |
| Y66H, Y145F | P4-3 | Φ = 0.3 ε = 22,300 | 382 446 | 51 | 64 |
| Y66H | BFP | Φ = 0.24 ε = 21,000 | 384 448 | 15 | 59 |
| Y66W type | | | | | |
| S65A, Y66W, S72A N146I, M153T, V163A | W1C | Φ = 0.39 ε = 21,200 | 435 495 | 100 | 82 |
| F64L, S65T, Y66W, N146I, M153T, V163A | W1B | Φ = 0.4 ε = 32,500 | 434 452 476 (505) | 80 | 71 |
| Y66W, N146I, M153T, V163A | hW7 | Φ = 0.42 ε = 23,900 | 434 452 476 (505) | 61 | 88 |
| Y66W | | | 436 485 | N.D. | N.D. |
| T203Y type | | | | | |
| S65G, S72A, K79R, T203Y | Topaz | Φ = 0.60 ε = 94,500 | 514 527 | 100 | 14 |
| S65G, V68L, S72A T203Y | 10C | Φ = 0.61 ε = 83,400 | 514 527 | 58 | 21 |
| S65G, V68L, Q69K S72A, T203Y | h10C+ | Φ = 0.71 ε = 62,000 | 516 529 | 50 | 54 |

TABLE 1-continued

| Mutations | Common Name | Quantum Yield (Φ) & Molar Extinction (ε) | Excitation & Emission Max | Relative Fluorescence At 37° C. | Sensitivity To Low pH % max F at pH 6 |
|---|---|---|---|---|---|
| S65G, S72A, T203H | | Φ = 0.78 ε = 48,500 | 508 518 | 12 | 30 |
| S65G, S72A T203F | | Φ = 0.70 ε = 65,500 | 512 522 | 6 | 28 |
| T203I type | | | | | |
| T203I, S72A, Y145F | Sapphire | Φ = 0.64 ε = 29,000 | 395 511 | 100 | 90 |
| T203I T202F | H9 | Φ = 0.6 ε = 20,000 | 395 511 | 13 | 80 |

As previously, cleavage of the protein of interest by a protease results in an alteration in energy transfer between the specific binding partner bound fluorescent ligand and the fluorescent protein that may be used to detect protease activity. Again, the fluorescent moieties are typically chosen such that the excitation spectrum of one of the moieties (the acceptor fluorescent moiety) overlaps with the emission spectrum of the donor fluorescent moiety.

A contemplated version of the method is to use inducible controlling nucleotide sequences to produce a sudden increase in the expression of either the specific binding partner-fusion protein or the post-translational activity being assayed, e.g., by inducing expression of the construct. A post-translational activity could be expressed within the cell, or induced, or introduced using a membrane translocating sequence (Rojas et al., (1998) Nature Biotech 16 370–375) if did not naturally occur in that cell. The efficiency of FRET is monitored at one or more time intervals after the onset of increased expression of the post-translational activity.

Alternatively the post-translational activity could be monitored one or more times after the addition of a stimulus, such as an agonist, antagonist or test chemical. For example, for use in drug screening assays to identify compounds that alter a post translational activity. In another embodiment, the ability of a test chemical to alter a post-translational activity, in a cell-based assay may be determined. In these assays, cells transfected with an expression vector encoding a specific binding partner fused to a protein of interest, as described above are exposed to different amounts of the test chemical, and the effect on FRET or fluorescence polarization in each cell can be determined before or after exposure of a stimulus. Typically, as with any method of the present invention, the difference in FRET or polarization of treated cells is compared to that of untreated controls.

The methods of the present invention can also take place in vivo, such that compounds and test chemicals are administered to an animal or transgenic organism rather than the procedure taking place in culture or using samples from an organism.

A System for Spectroscopic Measurements

The fluorescent ligand/specific binding partner systems of the present invention can be used with a system for spectroscopic measurement, comprising: a reagent for an assay, and a device comprising at least one plate or container, preferably a multi-well platform, and a second platform to hold said plate or container for detecting a signal from a sample. The system can further comprise a detector, such as a detector appropriate for detecting a signal from a sample or a plate on in a container as such detectors are known in the art or are later developed. The system can comprise multiple plates or containers or multi-well platforms. In this context, a reagent for an assay includes any reagent useful to perform biochemical or biological in vitro or in vivo testing procedures, such as, for example, buffers, co-factors, proteins such as enzymes or proteases, carbohydrates, lipids, nucleic acids, active fragments thereof, organic solvents such as DMSO, chemicals, analytes, therapeutics, compositions, cells, antibodies, ligands, and the like. In this context, an active fragment is a portion of a reagent that has substantially the activity of the parent reagent. The choice of spectroscopic probe/ligand conjugate—specific binding partner pair depends on the type of assay to be performed. For example, FRET based assays would typically comprise a specific binding partner with fused to a fluorescent protein, or containing a binding site for a second fluorophore. Fluorescent polarization based assays would typically be completed with specific binding partners comprising one a fusion protein to a protein of interest. In both cases assays would typically be run with cells.

The fluorescent substrates of the present invention are suited for use with systems and methods that utilize automated and integratable workstations for identifying modulators, and chemicals having useful activity. Such systems are described generally in the art (see, U.S. Pat. No. 4,000, 976 to Kramer et al. (issued Jan. 4, 1977), U.S. Pat. No. 5,104,621 to Pfost et al. (issued Apr. 14, 1992), U.S. Pat. No. 5,125,748 to Bjornson et al. (issued Jun. 30, 1992), U.S. Pat. No. 5,139,744 to Kowalski (issued Aug. 18, 1992), U.S. Pat. No. 5,206,568 Bjornson et al. (issued Apr. 27, 1993), U.S. Pat. No. 5,350,564 to Mazza et al. (Sep. 27, 1994), U.S. Pat. No. 5,589,351 to Harootunian (issued Dec. 31, 1996), and PCT Application Nos: WO 93/20612 to Baxter Deutschland GMBH (published Oct. 14, 1993), WO 96/05488 to McNeil et al. (published Feb. 22, 1996), WO 93/13423 to Agong et al. (published Jul. 8, 1993) and PCT/US98/09526 to Stylli et al., filed May 14, 1998.

Typically, such a system includes: A) a storage and retrieval module comprising storage locations for storing a plurality of chemicals in solution in addressable chemical wells, a chemical well retriever and having programmable selection and retrieval of the addressable chemical wells and having a storage capacity for at least 100,000 addressable wells, B) a sample distribution module comprising a liquid handler to aspirate or dispense solutions from selected addressable chemical wells, the chemical distribution module having programmable selection of, and aspiration from, the selected addressable chemical wells and programmable dispensation into selected addressable sample wells (including dispensation into arrays of addressable wells with different densities of addressable wells per centimeter squared) or at locations, preferably pre-selected, on a plate, C) a sample transporter to transport the selected addressable chemical wells to the sample distribution module and optionally having programmable control of transport of the selected addressable chemical wells or locations on a plate (including adaptive routing and parallel processing), D) a reaction module comprising either a reagent dispenser to dispense reagents into the selected addressable sample wells or locations on a plate or a fluorescent detector to detect chemical reactions in the selected addressable sample wells or locations on a plate, and a data processing and integration module.

The storage and retrieval module, the sample distribution module, and the reaction module are integrated and programmably controlled by the data processing and integration module. The storage and retrieval module, the sample distribution module, the sample transporter, the reaction module and the data processing and integration module are operably linked to facilitate rapid processing of the addressable sample wells or locations on a plate. Typically, devices of the invention can process at least 100,000 addressable wells or locations on a plate in 24 hours. This type of system is described in U.S. Ser. No. 08/858,016 by Stylli et al., filed May 16, 1997, entitled "Systems and method for rapidly identifying useful chemicals in liquid samples."

If desired, each separate module is integrated and programmably controlled to facilitate the rapid processing of liquid samples, as well as being operably linked to facilitate the rapid processing of liquid samples. In one embodiment the invention provides for a reaction module that is a fluorescence detector to monitor fluorescence. The fluorescence detector is integrated to other workstations with the data processing and integration module and operably linked with the sample transporter. Preferably, the fluorescence detector is of the type described herein and can be used for epi-fluorescence. Other fluorescence detectors that are compatible with the data processing and integration module and the sample transporter, if operable linkage to the sample transporter is desired, can be used as known in the art or developed in the future. For some embodiments of the invention, particularly for plates with 96, 192, 384 and 864 wells per plate, detectors are available for integration into the system. Such detectors are described in U.S. Pat. No. 5,589,351 (Harootunian), U.S. Pat. No. 5,355,215 (Schroeder), U.S. patent application (serial number pending), entitled "Detector and Screening Device for Ion Channels" filed Jul. 17, 1998, and PCT patent application WO 93/13423 (Akong). Alternatively, an entire plate may be "read" using an imager, such as a Molecular Dynamics Fluor-Imager 595 (Sunnyvale, Calif.). Multi-well platforms having greater than 864 wells, including 3,456 wells, can also be used in the present invention (see, for example, the PCT Application PCT/US98/11061, filed Jun. 6, 1998. These higher density well plates require miniaturized assay volumes that necessitate the use of highly sensitivity assays that do not require washing. The present invention provides such assays as described herein.

EXAMPLES

Example I

Plasmids and Cell Transfection

The cDNA encoding the sFv (25 kDa protein) with two c-myc epitopes was amplified by polymerase chain reaction using the plasmid pHook-1 (Chestnut et al., J. Immunol. Method. 193:17–27 (1996)) (Invitrogen) as template, with sense primer (5' GGAATTCGCCGAGGTCAAGCTGCAG-GAG 3')(SEQ ID No:2) containing an EcoR1 site and antisense primer (5'GCTCTAGACTGGCCCACAGCAT-TCAGATCCTC 3')(SEQ ID No:3 containing Xba I site. For ER and trans-Golgi targeting, the cDNA was subcloned at EcoR I and Xba1 restriction sites in the expression plasmid pCDNA3.1 containing the specific targeting sequences (ER: preprolactin signal sequence and C-terminal SEKDEL) (SEQ ID No:9), trans-Golgli: amino acids 1 to 47 of the human beta-1,4-galactosyltransferase). Plasma membrane targeting was achieved with the pHook plasmid. CHO cells (ATCC CRL 9618) were transfected with plasmids encoding targeted sFv using lipofectamine (Gibco) as is known in the art.

Example II

Synthesis of Hapten-Fluorophore Conjugates

A flexible aliphatic linker was added to 4-ethoxymethylene-2-phenyl-2-oxazolin-5-one (phOx) (Sigma) by reaction of 50 mg phOx with 14.3 µl 1,5-diaminopentane (Aldrich) in 2.5 ml acetone for 1 h. The di-substituted aminopentane was precipitated by addition of two volumes of 50 mM borate buffer (pH 9.2) leaving the product in solution. A more rigid trans-cyclohexane linker was added to phOx by reaction of trans-1,4-diaminocyclohexane (Aldrich) (5.1 mg in 0.5 ml of DMSO) and phOx (10 mg in 0.5 ml acetone) for 2 h. The di-substituted diaminocyclohexane was precipitated by addition of an equal volume of water, leaving the monosubstituted diaminocyclohexane in solution. PhOx-Bodipy® F1 was prepared by reaction of excess Bodipy® FL succinimidyl ester (Molecular Probes) with 1 mM of phOx-aminopentane in borate buffer for 2 h. The product was obtained as a precipitate. PhOx-tetramethylrhodamine was prepared by reaction of excess tetramethylrhodamine succinimidyl ester (Molecular Probes) with 5 mM phOx-aminocyclohexane in borate buffer for 6 h. The product was obtained as a precipitate. PhOx-fluorescein was prepared by reaction of equimolar amounts of phOx (0.5 mg in 25 µl acetone) and fluorescein cadaverine (Molecular Probes) (1 mg in 50 µl dimethylformamide) for 1 h. PBS was added, unreacted phOx was removed by hexane extraction, and the product was extracted with butanol. PhOx-ethanolamine was prepared by reaction of 1 mg phOx with 0.3 µl ethanolamine in 10 ml ethanol for 1 h. All reactions were conducted at room temperature. Products were judged to be greater than 95% pure by TLC and compounds were confirmed by mass spectrometry using well-known methods.

Example III

Fluorescence Measurements

Cells were labeled at two days after transfection, with phOx-fluorophore conjugates by incubation with low concentrations (<100 nM) of the conjugates. Unless otherwise indicated, cells were observed in the absence of the conjugate in the bathing media. Images were recorded at room temperature on a K2 BIO microscope (Technical Instruments) equipped with a 60× PlanApo objective (Nikon, N. A. 1.4), coaxial-confocal attachment, and cooled CCD camera (Photometrics). Dual-excitation ratio images of fluorescein were acquired using 440 and 490 nm excitation filters and a 520 nm long pass emission filter (Chroma). Continuous recordings of the fluorescence time course were obtained on a Nikon Diaphot epifluorescence microscope equipped with a 100× PlanApo objective (Nikon, N. A. 1.4), a photomultiplier using a 530 nm bandpass emission filter and an optical filter changer (Model 10-C, Sutter Instrument Co.) containing 440 and 490 nm excitation filters. Cuvette fluorescence measurements were conducted on an SLM 8000c fluorometer (SLM Aminco). Spectra were recorded with 4 nm slit widths; time courses were acquired with 495 nm excitation and a 510 mm longpass emission filter.

Example IV

Cell Labeling Using PhOx in CHO Cells

Figure 2:
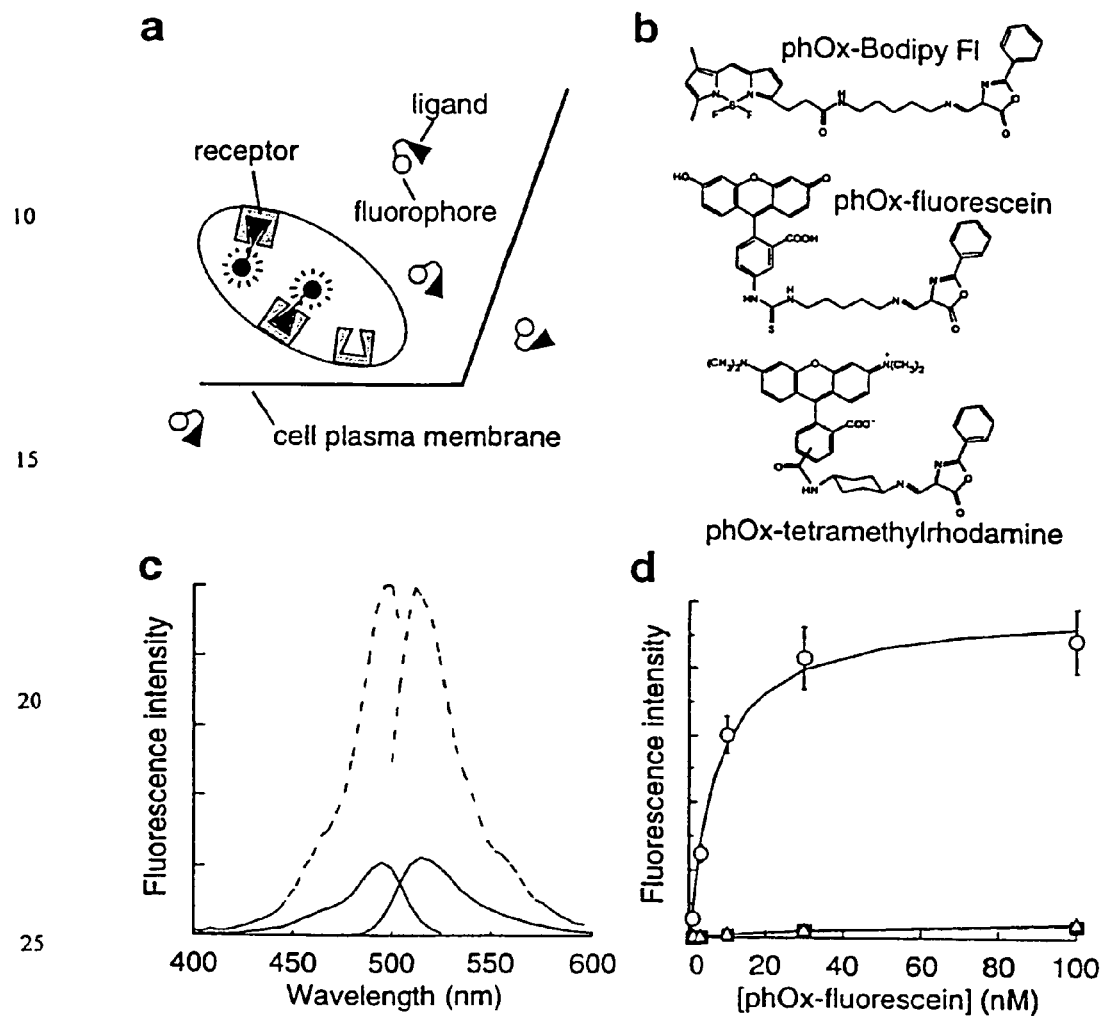
FIG. 2A represents one strategy for fluorophore targeting. A single-chain antibody, specific binding partner, is targeted to an intracellular site by cDNA transfection. Ligand-fluorophore conjugate added to the media is trapped by the specific binding partner. Fluorescence in the cell increases upon binding to the specific binding partner.
In FIG. 2B, chemical structures of preferred conjugates are shown.
FIG. 2C and FIG. 2D represent fluorescence and biding affinity of phOx-fluorescein.

A cell labeling method was developed that combines the site specificity conferred by genetically encoded protein targeting sequences with the spectral and indicator properties of fluorophores. The strategy is to express a high affinity specific binding partner at a specified intracellular location to trap a conjugate of an indicator linked to a specific ligand (FIG. 2A). We chose a single-chain antibody (Chesnut, supra, 1996) (sFv) as the specific binding partner, and a high affinity hapten (phOx) as the ligand. Although many receptor-ligand pairs are possible, the antibody-hapten pair used here was chosen because of the simple ligand-probe chemistry and high affinity interaction without interference from cellular factors. For sFv targeting, cells are transfected with cDNAs encoding sFv in fusion with Golgi, ER or plasma membrane targeting sequences. Fluorophore-hapten conjugates were added to the extracellular solution at low concentrations, diffused to sites of sFv expression, and bound to the sFv. Conjugates of different indicator, spectral and linker properties were synthesized (FIG. 2B), including phOx-Bodipy® FL (green fluorescent, flexible linker), phOx-fluorescein (green fluorescent, pH-sensitive, flexible linker), and phOx-tetramethylrhodamine (red fluorescent, rigid linker). The flexible linkers were designed to permit stacking of the unbound hapten with its covalently attached fluorophore to form a dark (non-fluorescent) complex.

The sFv/hapten-fluorophore system preferably include: bright fluorescence of the bound hapten-fluorophore conjugate, high affinity biding of the conjugate to sFv, strong cellular expression of functional sFv, membrane permeability of the conjugate, and minimal cellular toxicity. These characteristics were fulfilled for cellular sFv expression (using the Golgi, ER and plasma membrane vectors) and binding of the hapten-fluorophore conjugates in FIG. 2B. Fluorescence spectra of phOx-fluorescein bound to sFv and of an equal concentration of unbound phOx-fluorescein in solution had similar spectral shape (FIG. 2C). As intended, the fluorescence of the unbound conjugate was decreased considerably (by 5-fold) over that of the bound conjugate. Images of CHO cells expressing sFv at the plasma membrane were acquired with increasing concentration of phOx-fluorescein. The fluorescence from sFv-bound phOx-fluorescein was used to determine a dissociation constant ($K_d$) of 6.8 nM (FIG. 2D). This agrees with the value of 5.5 nM obtained in CHO cell suspensions expressing sFv at the plasma membrane (not shown). At 10 nM phOx-fluorescein, fluorescence from free dye was 75 times lower than that of bound dye. No significant fluorescence from non-sFv expressing cells was seen.

The toxicity and stability of the conjugates were investigated. There were no differences in cell growth as assessed by cell counting and viability as assessed by Trypan Blue exclusion between control cells and cells incubated for 24 hours with 200 nM of each conjugate. The stability of the imine bond in the conjugates was determined in cells. In freshly prepared phOx-fluorescein and phOx-fluorescein incubated with cell suspensions for up to 7 hours, the imine bond was hydrolyzed in 0.5 M NaOH, resulting in increased fluorescence. The fluorescence increase after treatment with NaOH was the same in both samples, indicating that the imine bond was not hydrolyzed in cells.

Figure 3:
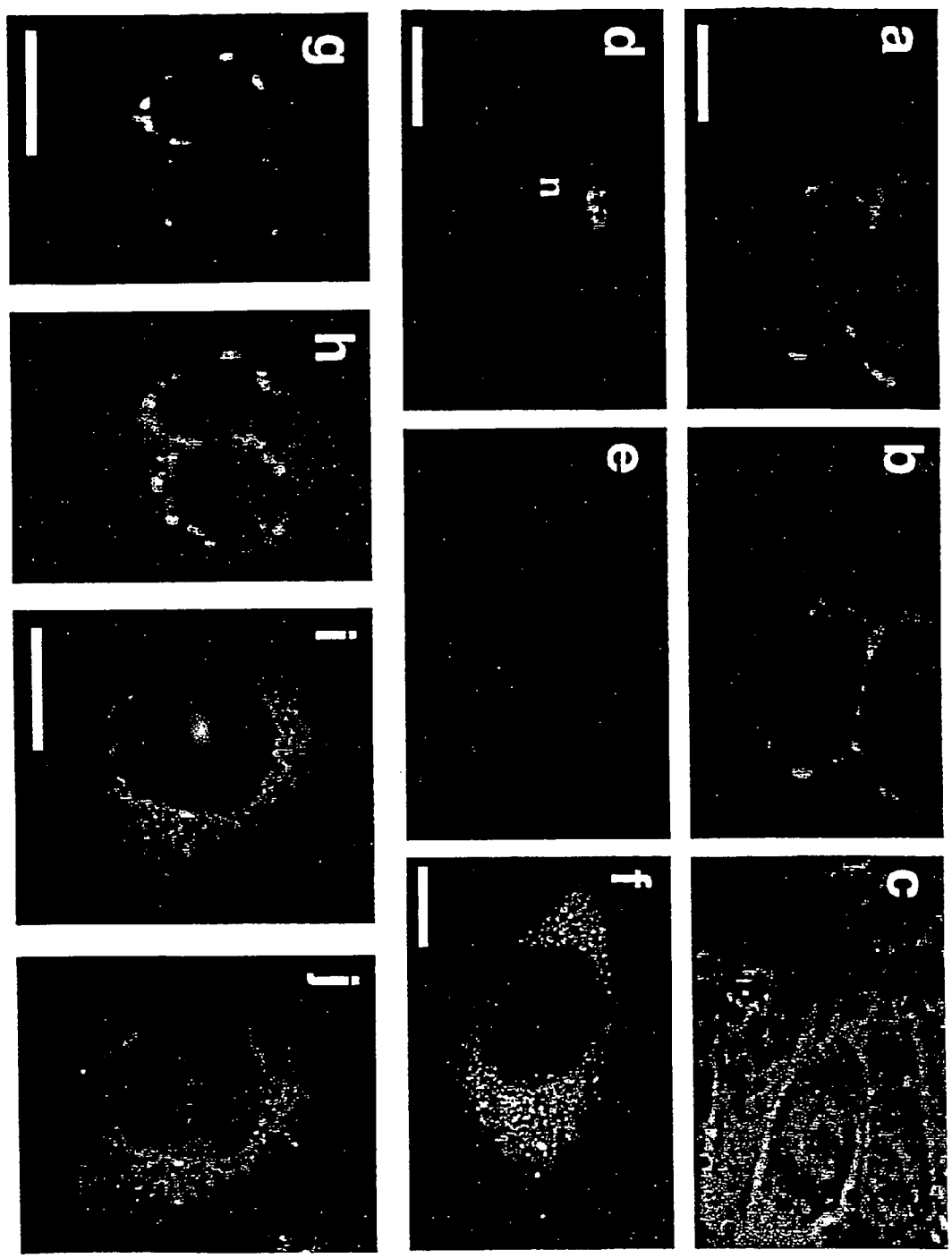
FIG. 3 represents site-specific labeling of CHO cells.

The various sFv targeting constructs and phOx conjugates were studied in CHO cells. FIG. 3A shows a fluorescence image of living cells expressing the sFv at the plasma membrane and stained with phOx-rhodamine. A plasma membrane staining pattern was found. FIG. 3B shows staining of sFv in the same cells with a fluorescein-labeled anti-c-myc antibody. Comparison with FIG. 3A demonstrates that only sites of sFv expression were significantly labeled with phOx-rhodamine. There was no significant staining of adjacent cells that did not express sFv (FIG. 3C). FIG. 3D shows specific phOx-Bodipy® staining of Golgi. Staining was reversed by addition of 1 µM phOx-ethanolamine (FIG. 3E). FIG. 3F shows phOx-Bodipy® staining of ER, seen as a characteristic reticular pattern. The high expression level of the sFv, the relatively high affinity of the hapten/sFv, and the low fluorescence of the unbound conjugate allowed images to be obtained in the presence of <10 nM concentrations of unbound conjugate with little contribution from free conjugate. For quantitative measurement of organelle pH, the free dye was washed out of the bathing solutions. Leakage out of the Golgi, which required dissociation from the sFv and diffusion through lipid membranes and unstirred layers, had a half time of tens of minutes.

The subcellular location of expressed sFv was confirmed by immunofluorescence. Cells transfected with the Golgi-sFv construct showed perinuclear staining by a fluorescein-labeled, anti-c-myc antibody (FIG. 3G) which co-localized with staining by antibodies against the Golgi marker 58 k protein (FIG. 3H). Cells transfected with the ER-sFv construct showed a reticular staining pattern with the c-myc antibody (FIG. 3I) which co-localized with staining by fluorescein labeled concavalin A, an ER marker (FIG. 3J). The membrane permeability of the conjugates was high enough to load cells by incubation at 37° C. for 4 hours for phOx-fluorescein, 2 hours for phOx-rhodamine, or 10 minutes for the less polar phOx-Bodipy®. Cells could be loaded at 4° C., indicating that the conjugate entered the cells primarily by transmembrane diffusion and not by endocytosis. These results demonstrate the selective targeting of fluorescent probes to expressed sFv in living cells.

Figure 4:
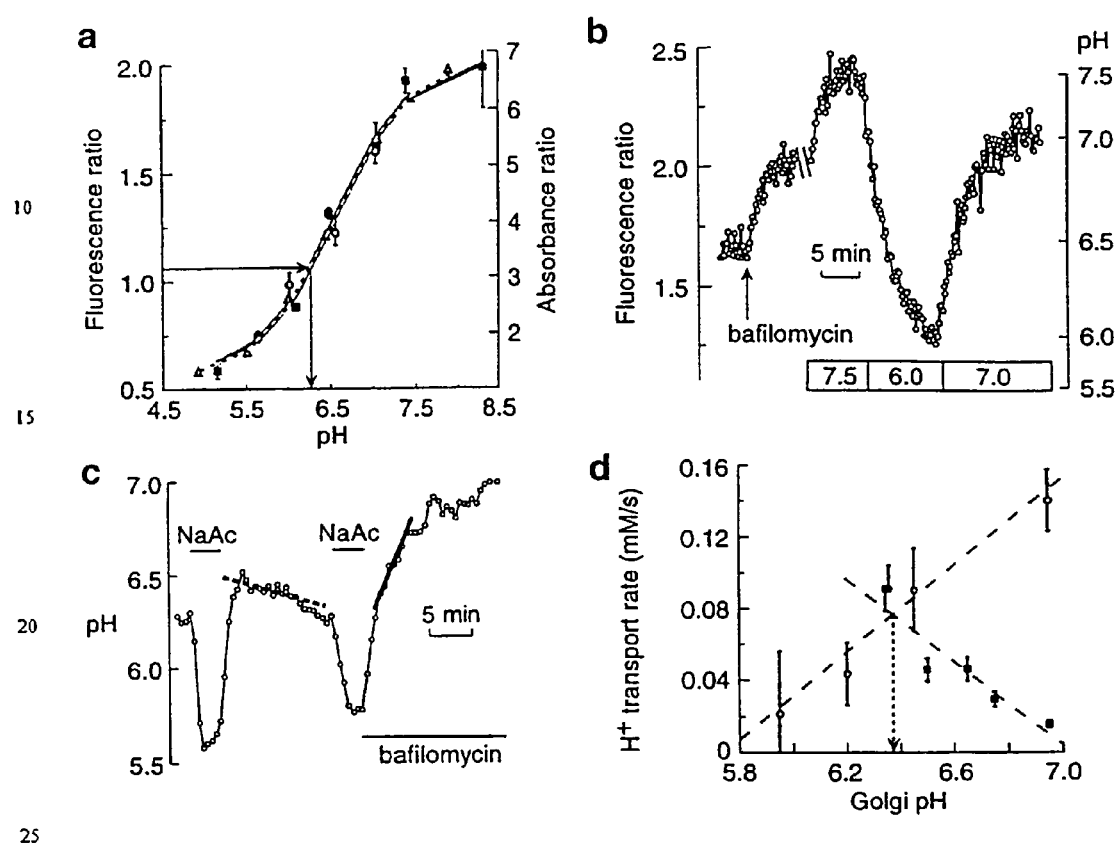
FIG. 4 represents the measurement of Golgi pH.

Organelle-specific sFv targeting was applied to measure Golgi pH using phOx-fluorescein as the probe. Ratio images were calculated from images of Golgi labeled with phOx-fluorescein acquired at 440 nm and 490 nm excitation wavelengths. To convert ratios to absolute pH, cells were perfused with "calibration buffers" at different pH containing high K+ and the ionophore monensin to equalize extracellular and Golgi lumenal pH (Kim et al., J. Cell Biol. 134:1387–1399 (1996)). The dependence of the fluorescence ratio on pH was measured for Golgi and plasma membrane-expressed sFv (FIG. 4A). The apparent $pK_a$ of 6.56 of bound phOx-fluorescein was not different from that of unbound phOx-fluorescein in solution ($pK_a$=6.54). The average Golgi fluorescence ratio of 1.05±0.05 corresponds to a pH of 6.25±0.06, in agreement with previous estimates (Kim et al., supra, 1996; Seksek et al., J. Biol. Chem. 270:49674970 (1995)).

The Golgi-targeted phOx-fluorescein was used to detect continuous changes in lumenal pH in individual cells. FIG. 4B shows that the fluorescence ratio increases upon addition of the vacuolar $H^+$ pump inhibitor bafilomycin $A_1$. The ratios measured using calibration buffers were used to convert fluorescence ratios to pH (scale at right). Golgi pH initially at ~6.3 promptly alkalinized after the addition of bafilomycin $A_1$.

It has been proposed that the steady-state Golgi pH is determined thermodynamically by the free energy of ATP hydrolysis used by the vacuolar H+/ATPase to pump H+ against an electrochemical gradient (Rybak et al. Biophys. J. 73: 674–87 (1997)). To test the model prediction that the $H^+$ pump rate is zero at steady-state pH, the rates of Golgi $H^+$ pump and leak were measured as a function of Golgi lumenal pH. After Golgi alkalinization by a 20 mM Na acetate pre-pulse, H+ pumping into the Golgi restores steady-state pH (FIG. 4C). The initial rate of pH change (dashed line) is the difference between pump and leak rates: $dpH/dt = (dH^+/dt_{leak} - dH^+/dt_{pump})/\beta$. The buffer capacity, $\beta$, was measured by the $NH_4Cl$ pulse method (Roos and Boron Physiol. Rev. 61, 296421 (1981)) to be constant (38±3 mM/pH units) in the pH range 6–7 (not shown). The $H^+$ leak rate, $dH^+/dt_{leak}$, was measured from the pH change (solid line, FIG. 4C) after an identical 20 mM Na acetate pre-pulse with the $H^+$ pump inhibited by bafilomycin $A_1$. Similar pre-pulse measurements were done at different Golgi pH by varying Na acetate and $NH_4Cl$ concentrations. FIG. 4D shows that computed $H^+$ pump rate increases sharply with Golgi pH, but that pump rate is not zero at the Golgi state-state pH of ~6.25. Although it is recognized that the pre-pulse method used to alter Golgi pH also alters cytoplasmic pH, it has been reported that the $H^+$ pump rate is relatively insensitive to cytoplasmic pH in both mammalian (Kim et al., supra, 1996) and plant (Davies et al. Proc. Natl. Acad. Sci. USA 91, 8547–8551 (1994)) systems.

In the steady-state $H^+$ pump rate must equal H+ leak rate. The dependence of the leak rate on Golgi pH was measured from the kinetics of pH change after bafilomycin $A_1$ addition as shown in FIG. 4B. The data for different pH are summarized in FIG. 4D, showing decreased $H^+$ leak as Golgi pH increases. The intersection of the $H^+$ pump and leak curves predicts correctly the observed steady-state Golgi pH, supporting a balanced pump/leak mechanism for setting Golgi pH. Thus, the resting pH is determined by the kinetics of proton leak versus pump. Shifts in the leak or pump curves could provide a simple mechanism for the observed differences in resting pH in organelles of the secretory pathway.

The specific binding partner-mediated probe targeting strategy should have numerous applications for the labeling of specified cellular structures with fluorescent or other indicator molecules. Specific binding partner-mediated targeting of chemical probes permits many types of measurements that cannot be made using GFP. Multiple fluorophores with excitation and emission wavelengths from the ultraviolet to the infrared can be targeted, permitting well-resolved multicolor fluorescence detection. For microscopy measurements on living cells, red and infrared probes are especially useful to minimize background autofluorescence, photodamage and photobleaching. As demonstrated in FIG. 3, bright fluorophores can be chosen with substantially improved molar absorbance and quantum yield over GFP. A unique application of specific binding partner-mediated probe targeting is the labeling of intracellular compartments with fluorescent indicators that are sensitive to pH (FIG. 4) ions (Ca++, Na+, Cl−) or membrane potential. Conjugates can also be designed to deliver magnetic resonance probes, caged compounds or chemical cross-linkers. Finally the use of cell-specific promoters and gene transfer should allow the in vivo targeting of hapten-probe complexes to specific cell types in multicellular organisms.

All publications, including patent documents and scientific articles, referred to in this application are incorporated by reference in their entirety for all purposes to the same extent as if each individual publication were individually incorporated by reference.

All headings are for the convenience of the reader and should not be used to limit the meaning of the text that follows the heading, unless so specified.

I claim:

1. A method for localizing a probe within a cell, the method comprising:
   a) providing a sample comprising a cell expressing a membrane bound polypeptide, said polypeptide comprising a single chain antibody and an organelle targeting sequence wherein said single chain antibody binds to a specific ligand, wherein the ligand is phOx, wherein the membrane is a Golgi membrane, an Endoplasmic Reticulum (ER) or a plasma membrane;
   b) contacting the sample of a) with a membrane permeant probe/ligand conjugate, the probe/ligand conjugate comprising:
      i) a probe moiety,
      ii) a ligand comprising phOx, and
      iii) a linker moiety coupling the probe to the ligand; and
   c) detecting the probe/ligand conjugate within the cell, thereby localizing the probe within the cell.

2. The method of claim 1, wherein the probe is a spectroscopic probe.

3. The method of claim 1, wherein the polypeptide is a fusion protein.

4. The method of claim 1, wherein the detecting comprises NMR imaging.

5. The method of claim 1, wherein the detecting comprises positron emission tomography.

6. The method of claim 1, wherein the detecting comprises locating the fluorescence characteristic of the fluorescent moiety within the cell.

7. The method of claim 1, wherein the detecting comprises fluorescence activated cell sorting.

8. The method of claim 1, wherein the cell is an eukaryotic cell.

9. The method of claim 1, wherein the cell is a mammalian cell.

10. The method of claim 1, further comprising:
    i) adding a stimulus to the cell and
    ii) detecting the probe/ligand conjugate, before and at least one time after addition of the stimulus.

11. The method of claim 2, wherein the detecting comprises detecting at least one optical property of the spectroscopic probe.

12. The method of claim 11, wherein the optical property is fluorescence emission.

13. The method of claim 11, wherein the optical property is fluorescence anisotropy.

14. A method for localizing a probe, the method comprising:
    a) providing a sample comprising a cell expressing a specific binding partner, wherein the binding partner is a recombinant membrane bound polypeptide, said polypeptide comprising a single chain antibody that specifically binds to phOx, wherein the membrane is a Golgi membrane, an Endoplasmic Reticulum (ER) or a plasma membrane:
    b) contacting the cell of a) with a probe/ligand conjugate, the probe/ligand conjugate comprising:
       i) a probe moiety,
       ii) a ligand comprising phOx, and
       iii) a linker moiety coupling the probe to the ligand, wherein the ligand and the specific binding partner bind non-covalently, and wherein the probe/ligand conjugate is membrane permeant,
    c) detecting the probe/ligand conjugate within the cell, thereby localizing the probe within the cell.

15. The method of claim 1, wherein the probe provides a more intense signal when the probe/ligand conjugate is bound to the single chain antibody than when it is unbound.

16. The method of claim 2, wherein the probe provides a more intense signal when the probe/ligand conjugate is bound to the single chain antibody than when is unbound.

17. The method of claim 1, wherein the single chain antibody is bound to a Golgi apparatus membrane or an endoplasmic reticulum membrane.

18. The method of claim 1, wherein the linker comprises diaminopentane.

19. The method of claim 1, wherein the cell is a living cell.

20. The method of claim 1, wherein the probe is a pH sensitive fluorescent probe.

* * * * *

SEQUENCE LISTING

```
<160> NUMBER OF SEQ ID NOS: 9

<210> SEQ ID NO 1
<211> LENGTH: 951
<212> TYPE: DNA
<213> ORGANISM: Artificial sequence
<220> FEATURE:
<223> OTHER INFORMATION: single chain antibody
<221> NAME/KEY: CDS
<222> LOCATION: (1)..(951)

<400> SEQUENCE: 1 atg gcc gag gtc aag ctg cag gag tca ggg gga ggc tta gtg cag cct      48
Met Ala Glu Val Lys Leu Gln Glu Ser Gly Gly Gly Leu Val Gln Pro
1               5                   10                  15 gga ggg tcc cgg aaa ctc tcc tgt gca gcc tct gga ttc act ttc agt      96
Gly Gly Ser Arg Lys Leu Ser Cys Ala Ala Ser Gly Phe Thr Phe Ser
            20                  25                  30
```

```
agc ttt gga atg cac tgg gtt cgt cag gct cca gag aag ggg ctg gag      144
Ser Phe Gly Met His Trp Val Arg Gln Ala Pro Glu Lys Gly Leu Glu
     35                  40                  45 tgg gtc gca tat att agt agt ggc agt agt acc atc tac tat gca gac      192
Trp Val Ala Tyr Ile Ser Ser Gly Ser Ser Thr Ile Tyr Tyr Ala Asp
 50                  55                  60 aca gtg aag gga cga ttc acc atc tcc aga gac aat ccc aag aac acc      240
Thr Val Lys Gly Arg Phe Thr Ile Ser Arg Asp Asn Pro Lys Asn Thr
 65                  70                  75                  80 ctg ttc ctg caa atg acc agt cta agg tct gag gac acg gtc atg tat      288
Leu Phe Leu Gln Met Thr Ser Leu Arg Ser Glu Asp Thr Val Met Tyr
                 85                  90                  95 tac tgt gca aga gat tac ggg gct tat tgg ggc caa ggg acc acg gtc      336
Tyr Cys Ala Arg Asp Tyr Gly Ala Tyr Trp Gly Gln Gly Thr Thr Val
            100                 105                 110 acc gtc tcc tca ggt gga ggc ggt tca ggc gga ggt ggc tct ggc ggt      384
Thr Val Ser Ser Gly Gly Gly Gly Ser Gly Gly Gly Gly Ser Gly Gly
            115                 120                 125 ggc gga tcg gac att gag ctc acc cag tct cca gca atc atg tct gca      432
Gly Gly Ser Asp Ile Glu Leu Thr Gln Ser Pro Ala Ile Met Ser Ala
130                 135                 140 tct cca ggg gag agg gtc acc atg acc tgc agt gcc agt tca gta         480
Ser Pro Gly Glu Arg Val Thr Met Thr Cys Ser Ala Ser Ser Val
145                 150                 155                 160 agg tac atg aac tgg ttc caa cag aag tca ggc acc tcc ccc aaa aga      528
Arg Tyr Met Asn Trp Phe Gln Gln Lys Ser Gly Thr Ser Pro Lys Arg
                165                 170                 175 tgg att tat gac aca tcc aaa ctg tct tct gga gtc cct gct cgc ttc      576
Trp Ile Tyr Asp Thr Ser Lys Leu Ser Ser Gly Val Pro Ala Arg Phe
            180                 185                 190 agt ggc agt ggg tct ggg acc tct tac tct ctc aca atc agc agc atg      624
Ser Gly Ser Gly Ser Gly Thr Ser Tyr Ser Leu Thr Ile Ser Ser Met
            195                 200                 205 gag gct gaa gat gct gcc act tac tac tgc cag cag tgg agt agt aac      672
Glu Ala Glu Asp Ala Ala Thr Tyr Tyr Cys Gln Gln Trp Ser Ser Asn
210                 215                 220 cca ctc acg ttc ggt gct ggg acc aag ctg gag ctg aaa cgg gcg gcc      720
Pro Leu Thr Phe Gly Ala Gly Thr Lys Leu Glu Leu Lys Arg Ala Ala
225                 230                 235                 240 gca gaa caa aaa ctc atc tca gaa gag gat ctg aat ggg gcc gtc gac      768
Ala Glu Gln Lys Leu Ile Ser Glu Glu Asp Leu Asn Gly Ala Val Asp
                245                 250                 255 gaa caa aaa ctc atc tca gaa gag gat ctg aat gct gtg ggc cag gac      816
Glu Gln Lys Leu Ile Ser Glu Glu Asp Leu Asn Ala Val Gly Gln Asp
            260                 265                 270 acg cag gag gtc atc gtg gtg cca cac tcc ttg ccc ttt aag gtg gtg      864
Thr Gln Glu Val Ile Val Val Pro His Ser Leu Pro Phe Lys Val Val
            275                 280                 285 gtg atc tca gcc atc ctg gcc ctg gtg gtg ctc acc atc atc tcc ctt      912
Val Ile Ser Ala Ile Leu Ala Leu Val Val Leu Thr Ile Ile Ser Leu
            290                 295                 300 atc atc ctc atc atg ctt tgg cag aag aag cca cgt tag                  951
Ile Ile Leu Ile Met Leu Trp Gln Lys Lys Pro Arg
305                 310                 315

<210> SEQ ID NO 2
<211> LENGTH: 316
<212> TYPE: PRT
<213> ORGANISM: Artificial sequence
<220> FEATURE:
```

-continued

<223> OTHER INFORMATION: single chain antibody

<400> SEQUENCE: 2

Met Ala Glu Val Lys Leu Gln Glu Ser Gly Gly Gly Leu Val Gln Pro
1               5                   10                  15

Gly Gly Ser Arg Lys Leu Ser Cys Ala Ala Ser Gly Phe Thr Phe Ser
            20                  25                  30

Ser Phe Gly Met His Trp Val Arg Gln Ala Pro Glu Lys Gly Leu Glu
        35                  40                  45

Trp Val Ala Tyr Ile Ser Ser Gly Ser Ser Thr Ile Tyr Tyr Ala Asp
    50                  55                  60

Thr Val Lys Gly Arg Phe Thr Ile Ser Arg Asp Asn Pro Lys Asn Thr
65                  70                  75                  80

Leu Phe Leu Gln Met Thr Ser Leu Arg Ser Glu Asp Thr Val Met Tyr
                85                  90                  95

Tyr Cys Ala Arg Asp Tyr Gly Ala Tyr Trp Gly Gln Gly Thr Thr Val
            100                 105                 110

Thr Val Ser Ser Gly Gly Gly Ser Gly Gly Gly Gly Ser Gly Gly
        115                 120                 125

Gly Gly Ser Asp Ile Glu Leu Thr Gln Ser Pro Ala Ile Met Ser Ala
130                 135                 140

Ser Pro Gly Glu Arg Val Thr Met Thr Cys Ser Ala Ser Ser Ser Val
145                 150                 155                 160

Arg Tyr Met Asn Trp Phe Gln Gln Lys Ser Gly Thr Ser Pro Lys Arg
            165                 170                 175

Trp Ile Tyr Asp Thr Ser Lys Leu Ser Ser Gly Val Pro Ala Arg Phe
        180                 185                 190

Ser Gly Ser Gly Ser Gly Thr Ser Tyr Ser Leu Thr Ile Ser Ser Met
    195                 200                 205

Glu Ala Glu Asp Ala Ala Thr Tyr Tyr Cys Gln Gln Trp Ser Ser Asn
210                 215                 220

Pro Leu Thr Phe Gly Ala Gly Thr Lys Leu Glu Leu Lys Arg Ala Ala
225                 230                 235                 240

Ala Glu Gln Lys Leu Ile Ser Glu Glu Asp Leu Asn Gly Ala Val Asp
            245                 250                 255

Glu Gln Lys Leu Ile Ser Glu Glu Asp Leu Asn Ala Val Gly Gln Asp
        260                 265                 270

Thr Gln Glu Val Ile Val Val Pro His Ser Leu Pro Phe Lys Val Val
    275                 280                 285

Val Ile Ser Ala Ile Leu Ala Leu Val Val Leu Thr Ile Ile Ser Leu
290                 295                 300

Ile Ile Leu Ile Met Leu Trp Gln Lys Lys Pro Arg
305                 310                 315

<210> SEQ ID NO 3
<211> LENGTH: 32
<212> TYPE: DNA
<213> ORGANISM: Artificial sequence
<220> FEATURE:
<223> OTHER INFORMATION: antisense primer containing Xba I site

<400> SEQUENCE: 3
gctctagact ggcccacagc attcagatcc tc                                    32

<210> SEQ ID NO 4
<211> LENGTH: 28

```
<212> TYPE: DNA
<213> ORGANISM: Artificial sequence
<220> FEATURE:
<223> OTHER INFORMATION: sense primer containing EcoR1

<400> SEQUENCE: 4
ggaattcgcc gaggtcaagc tgcaggag                                          28

<210> SEQ ID NO 5
<211> LENGTH: 5
<212> TYPE: PRT
<213> ORGANISM: Artificial sequence
<220> FEATURE:
<223> OTHER INFORMATION: localization sequence targeting the nucleus

<400> SEQUENCE: 5

Lys Lys Lys Arg Lys
1               5

<210> SEQ ID NO 6
<211> LENGTH: 26
<212> TYPE: PRT
<213> ORGANISM: Artificial sequence
<220> FEATURE:
<223> OTHER INFORMATION: localization sequence targeting the
      mitochondrion

<400> SEQUENCE: 6

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25

<210> SEQ ID NO 7
<211> LENGTH: 4
<212> TYPE: PRT
<213> ORGANISM: Artificial sequence
<220> FEATURE:
<223> OTHER INFORMATION: localization sequence targeting endoplasmic
      reticulum

<400> SEQUENCE: 7

Lys Asp Glu Leu
1

<210> SEQ ID NO 8
<211> LENGTH: 4
<212> TYPE: PRT
<213> ORGANISM: Artificial sequence
<220> FEATURE:
<223> OTHER INFORMATION: insertion into plasma membrane
<221> NAME/KEY: VARIANT
<222> LOCATION: (1)..(4)
<223> OTHER INFORMATION: any amino acid

<400> SEQUENCE: 8

Cys Cys Xaa Xaa
1
```

```
<210> SEQ ID NO 9
<211> LENGTH: 6
<212> TYPE: PRT
<213> ORGANISM: Artificial sequence
<220> FEATURE:
<223> OTHER INFORMATION: specific targeting sequences c-terminal

<400> SEQUENCE: 9

Ser Glu Lys Asp Glu Leu
1               5
```